United States Patent
Boss et al.

(10) Patent No.: US 8,741,658 B2
(45) Date of Patent: Jun. 3, 2014

(54) RAPID METHOD TO MEASURE CYANIDE IN BIOLOGICAL SAMPLES

(75) Inventors: Gerry Boss, La Jolla, CA (US); Vijay Sharma, La Jolla, CA (US); Matthew Brenner, Irvine, CA (US); Purnendu K. Dasgupta, Arlington, TX (US); William Curt Blackledge, Carlsbad, CA (US)

(73) Assignees: The Regents of the University of California, Oakland, CA (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 13/634,703

(22) PCT Filed: Mar. 15, 2011

(86) PCT No.: PCT/US2011/028542
§ 371 (c)(1),
(2), (4) Date: Sep. 13, 2012

(87) PCT Pub. No.: WO2011/116006
PCT Pub. Date: Sep. 22, 2011

(65) Prior Publication Data
US 2013/0005044 A1   Jan. 3, 2013

Related U.S. Application Data

(60) Provisional application No. 61/313,927, filed on Mar. 15, 2010.

(51) Int. Cl.
*G01N 21/78*   (2006.01)
*G01N 21/77*   (2006.01)
*G01N 33/52*   (2006.01)
*G01N 33/48*   (2006.01)

(52) U.S. Cl.
USPC ............. 436/109; 436/63; 436/84; 436/164; 436/169; 422/400; 422/420; 422/82.05; 422/82.09

(58) Field of Classification Search
USPC ............. 436/63, 73, 84, 106, 109, 164, 166, 436/169; 422/400, 420, 68.1, 82.05, 82.09; 540/145
See application file for complete search history.

(56) References Cited

U.S. PATENT DOCUMENTS

2008/0227746 A1* 9/2008 Boss et al. ............ 514/52
2008/0280372 A1  11/2008 Walker et al.
2009/0258429 A1* 10/2009 Raymo et al. ............ 436/109

FOREIGN PATENT DOCUMENTS

WO   WO2008/078092 A1   7/2008
WO   2012/136793   * 10/2012

OTHER PUBLICATIONS

Blackledge et al. Analytical Chemistry, vol. 82, Apr. 26, 2010, pp. 4216-4221.*
Broderick et al. Experimental Biol. Medicine, vol. 231, 2006, pp. 641-649.*
Baldwin, D.A. et al., "The Chemistry of Vitamin $B_{12}$ Part 20.[1] Diaquocobinamide : p$K$ Values and Evidence for Conformational Isomers," J. Chem. Soc. Dalton Trans., No. 1, pp. 217-223, 1983.

(Continued)

*Primary Examiner* — Maureen Wallenhorst
(74) *Attorney, Agent, or Firm* — Fenwick & West LLP

(57) ABSTRACT

A method and devices analyze for the presence of cyanide in samples using colorimetric analysis of samples after contacting with cobinamide or monocyanocohinapmide.

24 Claims, 38 Drawing Sheets

(56) References Cited

OTHER PUBLICATIONS

Blackledge, W.C., et al., "New Facile Method to Measure Cyanide in Blood," Anal. Chem. vol. 82, No. 10, pp. 4216-4221, May 15, 2010.

Chinaka, S. et al., "Simultaneous determination of cyanide and thiocyanate in blood by ion chromatography with fluorescence and ultraviolet detection," Journal of Chromatography B, vol. 713, pp. 353-359, 1998.

Ford, S.H. et al., "Separation and study of corrinoid cobalt-ligand isomers by high-performance liquid chromatography," Journal of Chromatography, vol. 536, pp. 185-191, 1991.

Gewitz, H.S. et al., "Cyanide Formation in Preparations from *Chlorella volgaris* Beijerinck: Effect of Sonication and Amygdalin Addition," Planta (Berl.), vol. 131, pp. 145-148, 1976.

Guilbault, G.G. et al., "Ultra Sensitive, Specific Method for Cyanide Using *p*-Nitrobenzaldehyde and o-Dinitrobenzene," Analytical Chemistry, vol. 38, No. 7, pp. 834-836, 1966.

Ishii, A. et al., "Determination of Cyanide in Whole Blood by Capillary Gas Chromatography with Cryogenic Oven Trapping," Analytical Chemistry, vol. 70, pp. 4873-4876, 1998.

Lindsay, A.E. et al., "Analytical techniques for cyanide in blood and published blood cyanide concentrations from healthy subjects and fire victims," Analytica Chimica Acta, vol. 511, pp. 185-195, 2004.

Lundquist, P. et al., "Cyanide Concentrations in Blood after Cigarette Smoking, as Determined by a Sensitive Flourimetric Method," Clin. Chem., vol. 33, No. 7, pp. 1228-1230, Jul. 1987.

Lundquist, P. et al., "Determination of Cyanide in Whole Blood, Erythrocytes, and Plasma," Clin. Chem., vol. 31, No. 4, pp. 591-595, Apr. 1985.

Lundquist, P. et al., "The origin of hydrogen cyanide in breath," Arch Toxicol, vol. 61, pp. 270-274, 1988.

Ma, J., et al., "Cobinamide-Based Cyanide Analysis by Multiwavelength Spectrometry in a Liquid Core Waveguide," Anal. Chem., vol. 82, No. 14, pp. 6244-6250, Jul. 15, 2010.

Patent Cooperation Treaty, International Search Report and Written Opinion, International Patent Application No. PCT/US2011/028542, Dec. 19, 2011, 11 Pages.

Patent Cooperation Treaty, International Preliminary Report on Patentability, International Patent Application No. PCT/US2011/028542, Sep. 27, 2012, 8 Pages.

Paul, B.D. et al., "Cyanide and Thiocyanate in Human Saliva by Gas Chromatography—Mass Spectrometry," Journal of Analytical Toxicology, vol. 30, pp. 511-515, Oct. 2006.

Pettigrew, A.R. et al., "Microdiffusion Method for Estimation of Cyanide in Whole Blood and Its Application to the Study of Conversion of Cyanide to Thiocyanate," Clin. Chem., vol. 19, No. 5, pp. 446-471, May 1973.

Sharma, V.S. et al., "Reactions of Nitric Oxide with Vitamin $B_{12}$ and Its Precursor, Cobinamide," Biochemistry, vol. 42, pp. 8900-8908, 2003.

Španěl, P. et al., "Acetone, ammonia and hydrogen cyanide in exhaled breath of several volunteers aged 4-83 years," J. Breath Res., vol. 1, No. 1, pp. L1-L4, Sep. 2007.

Španěl, P. et al., "The concentration distributions of some metabolites in the exhaled breath of young adults," J. Breath Res., vol. 1, No. 1, pp. 1-8, Sep. 2007.

Stamyr, K. et al., "Background levels of hydrogen cyanide in human breath measured by infrared cavity ring down spectroscopy," Biomarkers, vol. 14, No. 5, pp. 285-191, 2009.

Toida, T. et al., "Determination of Cyanide and Thiocyanate in Blood Plasma and Red Cells by High-Performance Liquid Chromatography with Flourometric Detection," Journal of Chromatography, vol. 308, pp. 133-141, 1984.

Tracqui, A. et al., "Determination of Blood Cyanide by HPLC-MS," Journal of Analytical Toxicology, vol. 26, No. 3, pp. 144-148, Apr. 2002.

Wang, T. et al., "Analysis of breath, exhaled via the mouth and nose, and the air in the oral cavity," J. Breath Res., vol. 2, No. 3, pp. 1-13, Sep. 2008.

Zelder, F.H., "Specific Colorimetric Detection of Cyanide Triggered by a Conformational Switch in Vitamin $B_{12}$," Inorganic Chemistry, vol. 47, No. 4, pp. 1264-1266, Feb. 2008.

\* cited by examiner

RAPID METHOD TO MEASURE CYANIDE IN BIOLOGICAL SAMPLES

CROSS REFERENCE TO RELATED APPLICATIONS

The application is the 35 USC §371 national stage entry of PCT/US2011/028542 filed Mar. 15, 2011 and claims the benefit of U.S. Provisional Application 61/313,927 filed Mar. 15, 2010 which is hereby incorporated reference in its entirety for all purposes.

STATEMENT REGARDING FEDERALLY SPONSORED RESEARCH OR DEVELOPMENT

This invention was made with U.S. government support under AI064368 and NS058030 awarded by the National Institutes of Health. The U.S. government has certain rights in this invention.

FIELD

The disclosed method is related to colorimetric detection of cyanide in samples.

BACKGROUND

Cyanide is a rapidly acting toxin. It may be responsible for many of the 5,000-10,000 deaths due to smoke inhalation in the United States annually as it is released from the combustion of plastics, wool, and other nitrogen-containing materials. Large amounts of cyanide are used in a variety of industries, and, since it is toxic when inhaled or ingested, it could be used as a terrorist weapon.

A variety of methods exist for measuring cyanide in biological fluids including spectrophotometry, gas chromatography, fluorometry, gas chromatography-mass spectrometry, high performance liquid chromatography (HPLC), and HPLC-mass spectrometry. Spectrophotometric assays can analyze multiple samples relatively quickly, but lack sensitivity and specificity, while gas chromatography, mass spectrometry, and HPLC require expensive equipment and allow only limited sample throughput. Several existing methods require laborious multistep sample pre-treatment are not amenable for use in the field.

SUMMARY

Assays, methods and devices for detecting cyanide are disclosed. According to various embodiments, the assays use cobinamide or monocyanocobinamide to contact a sample. The sample is then analyzed colorimetrically. The colorimetric analysis can be qualitative or quantitative. In a qualitative analysis, a color change is observed indicating the presence of cyanide in the sample. Alternatively, absorbance of light by the sample at certain wavelengths indicates the presence of cyanide. The absorbance of light by the sample can also be used for quantitative analysis of cyanide in a sample. The detected absorbance by the sample is of light having a wavelength of about 300 nm to about 600 nm, about 348 nm, about 366 nm, about 490 nm to about 590 nm, about 505 nm, about 562 nm or about 580 nm. In another embodiment, the absorbance by the sample of light having about 366 run, about 562 nm, or about 580 nm and light having about 505 nm is measured. In one embodiment the sample is a biological sample such as blood, saliva or exhaled air. In another embodiment the sample is water.

DETAILED DESCRIPTION

Figure 1:
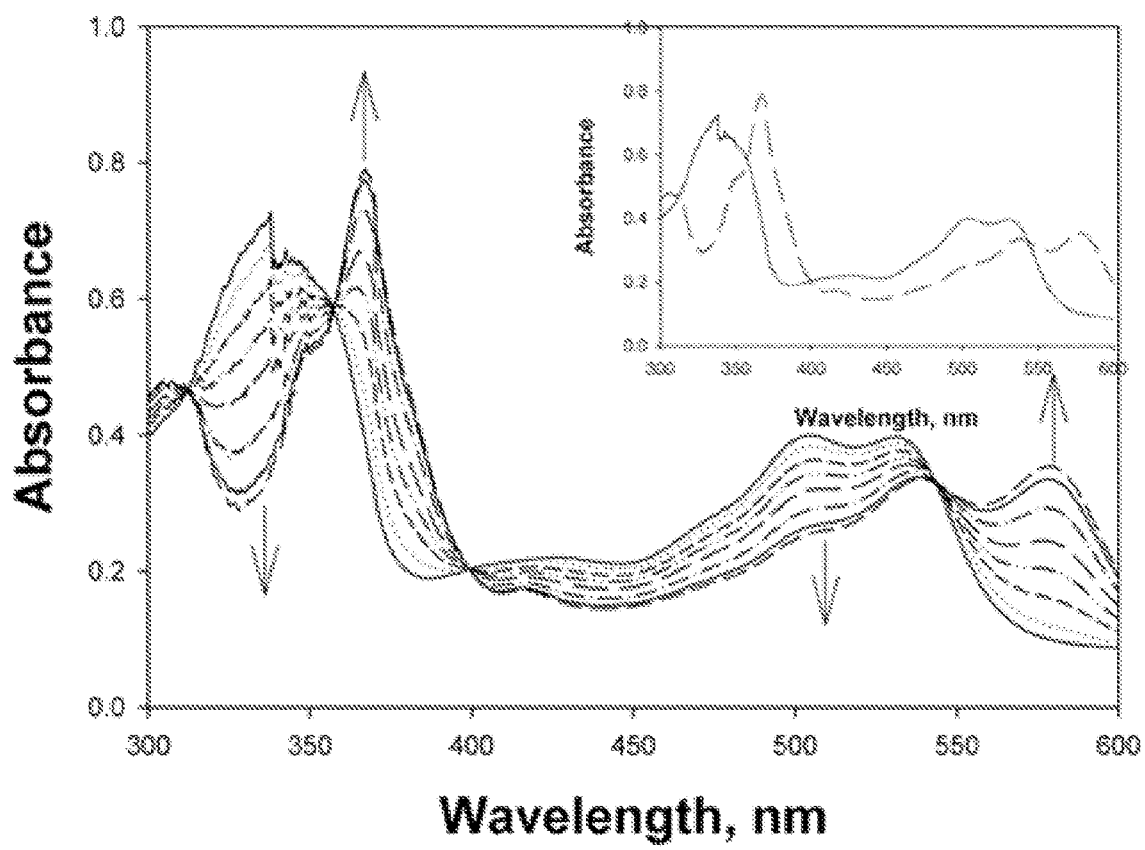
FIG. 1 illustrates the change in absorbance of dihydroxocobinamide as increasing amounts of cyanide are bound.

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "comprising a cell" includes one or a plurality of such cells, and so forth. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

All publications disclosed herein are incorporated by reference in their entirety for all purposes.

Cobinamide is an intermediate in the biosynthesis of cobalamin (vitamin $B_{12}$). At neutral pH, cobinamide exists as hydroxoaquocobinamide which has structure:

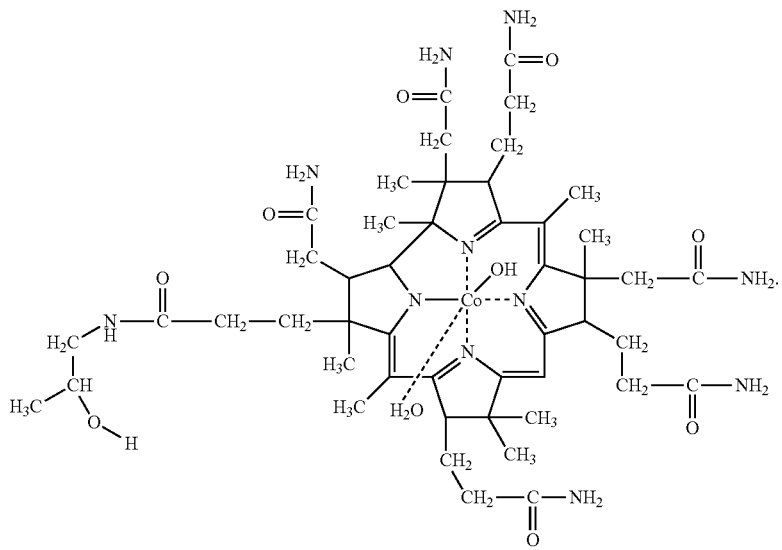

At pH>11, cobinamide exists as dihydroxocobinamide in which the water of the hydroxoaquocobinamide replaced by a second hydroxyl group. At acidic pH, cobinamide exists as diaquocobinamide in which the hydroxyl group of the hydroxoaquocobinamide is replaced by a second water. In this application, the term cobinamide refers to diaquocobinamide, hydroxoaquocobinamide and diaquocobinamide. To bind cyanide, the two coordination positions on cobalt in cobinamide that variously have water or hydroxyl groups, depending on pH, bind cyanide.

Hydroxoaquocobinamide has an overall cyanide binding affinity of $10^{22}$ $M^{-2}$ (first cyanide molecule binds with an affinity of $10^{14}$ $M^{-1}$, and second one with an affinity of $10^{8}$ $M^{-1}$). It binds cyanide with $10^{10}$ times greater affinity than cyanocobalamin, which has also been suggested for detection of cyanide by F. H. Zelder (*Inorg. Chem.* 2008, 47, 1264-1266). Spectral changes occur upon cyanide binding to cobinamide. Changes in single wavelengths, wavelength ratios, and wavelength range models accurately measured cyanide in biological samples. Cobinamide also undergoes a greater absorbance change than does any of the cobalamins and can thus be used for sensitive photometric measurement of cyanide, down to low μM levels. Furthermore, the qualitative color change is used to rapidly identify clinically relevant cyanide concentrations in blood.

The extremely high affinity of cobinamide for cyanide and the spectral changes that occur when cyanide binds to cobinamide were used to create an assay for detecting cyanide. The disclosed assays use both cobinamides and monocyanocobinamides. Monocyanocobinamides are any cobinamide in which one of the coordination positions around cobalt is taken by a cyanide ion. Monocyanocobinamides include aquocyanocobinamide and hydroxocyanocobinamide.

Cobinamide can be produced either by acid or base hydrolysis. Base hydrolysis of hydroxocobalamin to produce cobinamide is disclosed by Renz. (*Methods Enzymol.* 1971, 18c, 82-86) Acid hydrolysis of cobalamin to obtain cobinamide is disclosed in Broderick et al (*J Biol. Chem.*, 2005, 280, 8678-8685). In a preferred embodiment, cobinamide for use with the disclosed assays is produced using the base hydrolysis method.

The cobinamide or monocyanocobinamide are introduced into the sample through a solution or by impregnating a solid with the cobinamide or monocyanocobinamide. The solid can be paper such as filter paper, a membrane, or any other solid that is suitable for stably holding the cobinamide or monocyanocobinamide. The assay can be used in both a quantitative mode and a qualitative mode. For quantitation, the assay uses a spectrophotometer. LED's can be used as a light source as they are available in near monochromatic wavelengths. Other light sources commonly used with spectrophotometry can also be used, including lasers. Detectors include charge-coupled devices (CCD) and photodiode arrays as well as other light sensors. In a qualitative mode the assay is used by visually observing the color change in cobinamide-impregnated paper. Both methods have a high throughput capacity.

In addition to a high throughput capacity, other advantages of the cobinamide-based method are ease of use, stability of cobinamide, and application across a wide, adjustable dynamic range, depending on the cobinamide concentration used. In contrast to other colorimetric methods such as the NBA/DNB method, which requires two aromatic compounds and an unstable ether, the cobinamide-based method uses less toxic reagents having fewer environmental concerns. The qualitative assay detects a cyanide concentration >30 µM in clinical blood samples in 5 min at room temperature which is useful to rapidly identify cyanide-poisoned patients for early treatment and could easily be used in the field. The assay is made quantitative by using a hand-held spectrophotometer or light-emitting diodes.

In one embodiment, the analyzer uses flow reagent and sample injection coupled with a liquid core waveguide (LCW) flow cell. A charge coupled device (CCD) detector gives a multi-wavelength detection, which enables a data processing to increase the S/N. Parameters that affect the sensitivity and sample throughput, such as reaction matrix, flow rate and mixing coil length were investigated and optimized based on univariate experimental design. Under optimized conditions, the linear range is from 0 to 10 µM, with LOD from 0.03 to 0.04 µM for liquid phase cyanide at sample throughput higher than 30 h$^{-1}$. The relative standard deviations (R.S.D.) for repetitive determination of cyanide samples at 0.15, 0.5 and 1 µM were 7.6% (n=5), 3.2% (n=7) and 1.7% (n=6), respectively. High tolerance against common ions except for sulfide was achieved. The applicability of the method was demonstrated by analyzing fruit seeds (apple, pear and orange) and exhaled breath air samples. The percent recoveries range between 91 and 108%. Moreover, the LCW-based analyzer can be used as a universal device for samples of different matrix after a suitable pre-treatment procedure such as distillation or coupled with a gas collection device like diffusion scrubber.

Flow injection analysis (FIA), in which simultaneous injection of both sample and reagent in a technique commonly called zone penetration, has the advantage of using both reduced sample and reagent volumes. Less reagent volume is valuable as cobinamide is not commercially available. Additionally less reagent volume is valuable when reagents are expensive or toxic.

The LCW analyzer can be used for determination of cyanide in blood with the combination of a most commonly used Conway microdiffusion cell as disclosed in Lindsay, A. E., et al. (*Anal. Chim. Acta.*, 2004, 511, 185-195). The common ions have little to no effect on the very low level determination (2 µM) except for sulfide, which is eliminated by a suitable pre-treatment procedure.

When using FIA and LCW analyzer with aquocyanocobinamde an LOD of 8 nM, and linear dynamic range to 6 µM is achieved. The relative standard deviations of 50 and 100 nM samples were 0.49% (n=5) and 1.07% (n=5), respectively. The response base width for 1% carryover is <95 s, permitting a throughput of 40 samples/h. Spike recoveries in cyanide extracts from seeds and cyanide in saliva samples ranged from 91-104%.

In another embodiment, the sensitive and simple optical analyzer comprises an LED, high sensitive photodiode and impregnated filter. The linear range is from 0 to 180 µM depending upon sample volume (0.2, 0.5 and 1 mL), with LOD of 0.5 µM for 1 mL blood using dual wavelength detection in 5 min. The relative standard deviation (RSD) for repetitive determination of cyanide samples at 9 µM was 1.09% (n=5). When using the analyzer for the determination of cyanide in rabbit blood, the results showed good correlation (slope 1.05, $r^2$ 0.9257) with a standard microdiffusion-spectrophotometric method during a blind sample inter-comparison with independent calibration standards. Because of its ease of use, robustness, simplicity and low price, the analyzer can be used in the field for the determination of cyanide in blood sample at digital µM level without any pre-treatment.

In one embodiment analyses are performed at a pH above the $pK_a$ of cyanide. This minimizes loss of the cyanide to be measured as a gas which leads to more accurate analysis. This also is safer for those performing the analysis if the amount of cyanide to be detected is at a dangerously high level.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Cobinamide Synthesis. Cobinamide was synthesized from hydroxocobalamin acetate (Wockhardt, LTD, Mumbai, India) by base hydrolysis using cerium hydroxide (Renz, P. *Methods Enzymol.* 1971, 18c, 82-86); cerium hydroxide was produced by adding sodium hydroxide to cerium nitrate. The cobinamide product was purified on a carboxymethyl cellulose cation exchange column (CM52, Whatman), and concentrated and de-salted on a reversed-phase C-18 column. Final concentration was performed by flash evaporation and lyophilization; the cobinamide product is highly stable and can be stored for months at 4° C. Purity of cobinamide preparations was evaluated by HPLC by converting all of the cobinamide to dicyanocobinamide, and analyzing the sample on a C-18 reversed-phase column eluted with a gradient from 20 mM potassium phosphate, pH 4.6 containing 0.2 mM KCN (solvent A) to 60% methanol/water (solvent B): one minute to 40% B, 11 min to 50% B, and 1 min to I 00% B (flow rate 1 ml/min). The dicyanocobinamide eluted at 16 min and was detected by spectral absorption at 366 nm (Ford, S. H.; et al. *J.Chromatogr.* 1991, 536, 185-91). The concentration of cobinamide solutions was determined spectrophotometrically in 0.1 M HCl (as diaquocobinamide) using an extinction coefficient of 2.8×104/M/cm at 348 nm (Sharma, V. S., et al. *Biochemistry* 2003, 42, 8900-08). At neutral pH, cobinamide exists as hydroxoaquocobinamide, and at a pH of >11, it exists as dihydroxocobinamide (Baldwin, D. A., et al., *J. Chem. Soc. Dalton Trans.* 1983, 217-23).

Measurement of Cyanide Using a Standard Spectrophotometric Method. Cyanide was measured following the formation of o-nitrophenylhydroxylamine anion using p-nitrobenzaldehyde and o-dinitrobenzene as described by Guibault and Kramer (Anal. *Chem.* 1966, 28, 834-36) and modified by Gewitz et al. (*Planta* (Berl.) 1976, 131, 145-48) (this method is subsequently referred to as the NBA/DNB method). Briefly, potassium cyanide (Sigma-Aldrich) was dissolved in 0.1 M NaOH, and placed in tubes sealed with Kontes center well-appended stoppers with the wells containing 250 µl of collection fluid (0.1 M NaOH). Trichloroacetic acid (10%, 250 µl) was injected through the stoppers' septa into the samples, and the tubes were shaken at 37° C. for 60-75 min and then allowed to cool to room temperature. The released HCN was trapped in the collecting solution (pKa of HCN is 9.3). Freshly prepared reagent-grade p-nitrobenzaldehyde and o-dinitrobenzene in 2-methoxyethanol (NBA/DNB method) were added to the collection fluid followed by measurement of absorbance at 560 nm 10 min later.

Measurement of Cyanide Using Cobinamide. As shown in FIG. 1, on binding increasing amounts of cyanide, progressive changes occur in dihydroxocobinamide's absorbance spectrum between 300 and 600 nm until cobinamide is converted to the fully saturated dicyano form. Cobinamide concentrations from 5 to 100 µM could be used to allow for a wide dynamic range of cyanide concentrations. At the end of the 37° C. incubation, the 10 µM cobinamide-NaOH solution was analyzed spectrophotometrically over the range of 300-600 nm at 0.5 nm intervals using a Uvikon (Kontron 964) spectrophotometer. The ultraviolet/visible wavelength spectra of cobinamide (solid line) in 0.1 M NaOH is shown during transition to complexed dicyanocobinamide (dashed line). Serial addition of KCN to 25 µM cobinamide gradually changes the spectrum: shown are cyanide concentrations of 10 µM (dotted line), 20 µM (line with small dashes), 30 µM (line with small dashes and two dots), 40 µM (line with large dashes), 60 µM (line with small dashes and one dot), 80 µM (solid line) and 100 µM (line with large dashes); arrows indicate direction of change toward dicyanocobinamide. Inset shows dihydroxocobinamide (solid line) and dicyanocobinamide (dashed line).

Data Collection and MATLAB Program for Measuring Cyanide Using Cobinamide. To analyze wavelength ranges, anchoring spectra for cyanide-free dihydroxocobinamide (referred to as "A") and fully cyanide-bound dicyanocobinamide (referred to as "B") were obtained (FIG. 1). Given an experimental spectrum, $C(\lambda)$, a model spectrum, $M(\lambda)$, was defined as the linear combination of spectra $A(\lambda)$ and $B(\lambda)$ for the wavelength range of interest:

$$M(\lambda) = aA(\lambda) + bB(\lambda) \quad \text{(Equation 1)}$$

The coefficients a and b, sum to one. The coefficient b was solved whereby the sum of the squared differences of $M(\lambda)$ from $C(\lambda)$ was minimized for the wavelength range of interest. That is, the following expression was minimized:

$$\sum_\lambda (C(\lambda) - M(\lambda))^2$$

The following analytical solution for b (shown below in Equation 2) was utilized as part of a MATLAB program, whereby analysis of wavelength/absorbance datasets could be performed. For discrete wavelengths represented by index k, Equation 1 becomes the following:

$$M_k = (1-b)A_k + bB_k = A_k + b(B_k - A_k)$$

$$\varepsilon = \sum_k (C_k - A_k - b[B_k - A_k])^2$$

Minimizing with respect to b:

$$\partial \varepsilon / \partial b = \sum_k (C_k - A_k - b[B_k - A_k])(B_k - A_k) \equiv 0 \quad \text{(Equation 2)}$$

$$\Leftrightarrow \sum_k (C_k - A_k)(B_k - A_k) - b \sum_k (B_k - A_k)(B_k - A_k) = 0$$

$$\Leftrightarrow b = \frac{\sum_k (C_k - A_k)(B_k - A_k)}{\sum_k (B_k - A_k)^2}$$

Equation 2's solution of b provides the model-based absorbance "equivalent" for the range of interest, which, when plotted versus standard concentrations, may be used for concentration estimation in the same manner as for single wavelengths or wavelength ratios. Various single wavelengths, wavelength ratios, and wavelength ranges were evaluated. A MATLAB program was generated which simultaneously provided standard curves and cyanide measurements based on up to three range models, three wavelength ratios, and three single wavelength analyses.

Figure 2:
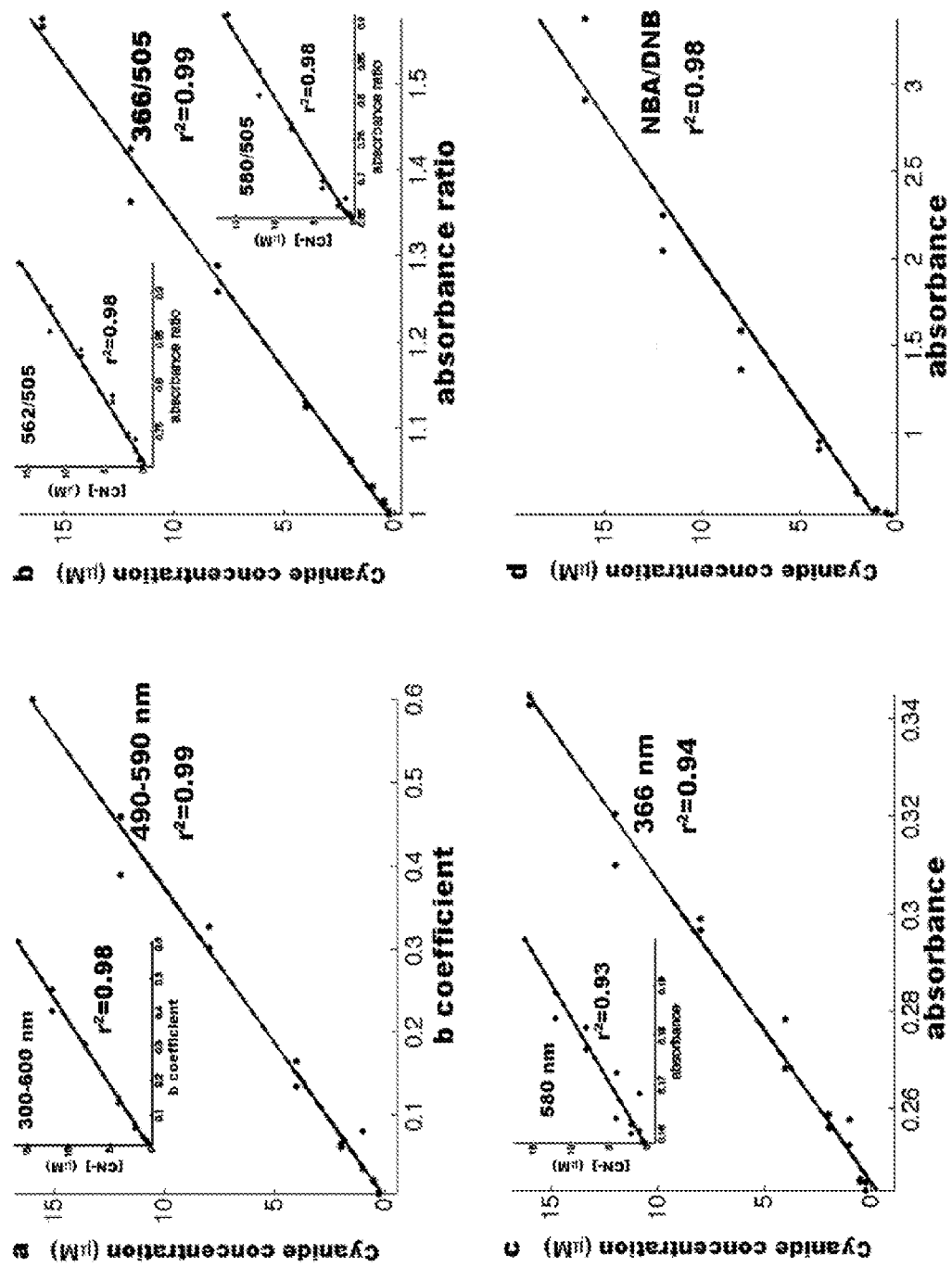
FIGS. 2a-d illustrate measurement of concentration of cyanide in 250 µl standard solutions over a range from 0.5 to 16 µM using both the cobinamide-based method and the NBA/DNB method.

Measurement of Cyanide in Standard Solutions. The concentration of cyanide in 250 µl standard solutions was measured over a range from 0.5 to 16 µM using both the cobinamide-based method and the NBA/DNB method (FIG. 2). For the cobinamide-based method, seven analyses of the data are presented, i.e., two range models (300-600 nm and 490-590 nm, panel a), three ratios (366/505, 562/505, and 580/505, panel b), and two single wavelengths (366 and 580 nm, panel c). Lines were generated by standard linear regressions. The 490-590 nm range analysis provided the best accuracy and precision over the range of 2-16 µM cyanide; this is based on having the lowest mean standard deviation (SD) of residua and highest mean correlation coefficient ($r^2$) with coefficients of variation and percent deviations from target <10% (Table 1). Cyanide concentrations of 2-16 µM were chosen to allow comparison with the NBA/DNB method that could reliably be used in this range (Table 1)

For both the 490-590 nm and 300-600 nm range analysis, the lower limit of quantitation was 2 µM (0.5 nmol), using a coefficient of variation and percent deviation from target value of <20%. By the same criteria, the three ratio analyses and NBA/DNB method were satisfactory at ≥4 µM (1 nmol) cyanide, while the cobinamide single wavelength analyses were useable at ≥8 µM (2 nmol) cyanide (Table 1).

For the range and ratio analyses, the limit of detection was found to be <1 µM (0.25 nmol) cyanide using the upper limit of noise as the mean plus three times the standard deviation of blank samples. The linear dynamic range of the assay is conservatively estimated to range from one-half to three times the cobinamide concentration for the ratio analyses; adjustment of the cobinamide concentration from 5-100 µM allows a linear dynamic range from <2.5 to >300 µM cyanide.

TABLE 1

Assessment of Accuracy and Precision of Measuring Cyanide Concentrations by a Cobinamide-Based Method and the NBA/DNB Method. The correlation coefficient ($r^2$), the standard deviation (SD) of the residua, and accuracy estimates are shown as means from ≥3 experiments. The precision and accuracy estimates are represented by coefficients of variation and mean percent deviation from target, respectively, in the range of 2-16 μM cyanide.

| analysis | $r^2$ | SD of residua | cyanide concentration | | | |
|---|---|---|---|---|---|---|
| | | | 2 μM | 4 μM | 8 μM | 16 μM |
| | | | coefficient of variation/% deviation from target | | | |
| wavelength range | | | | | | |
| 300-600 nm | 0.98 | 1.9 | 19/16 | 10/8.7 | 15/9.7 | |
| 490-590 nm | 0.99 | 1.8 | 9.5/8.3 | 6.3/5.0 | 7.6/5.8 | 5.8/3.3 |
| wavelength ratio | | | | | | |
| 366/505 | 0.99 | 1.4 | 22/18 | 12/8.6 | 4.3/3.5 | |
| 562/505 | 0.98 | 2.5 | 34/27 | 19/19 | 7.8/8.6 | 2.5/4.8 |
| 580/505 | 0.98 | 2.2 | 40/28 | 18/18 | 7.4/5.8 | 3.5/3.2 |
| single wavelength | | | | | | |
| 366 nm | 0.94 | 3.4 | 54/56 | 34/25 | 11/11 | |
| 580 nm | 0.93 | 4.7 | 58/47 | 38/27 | 20/16 | 13/10 |
| NBA/DNB method | 0.98 | 2.6 | 24/45 | 11/9.8 | 9.8/9.9 | 5.4/3.8 |

Measurement of Cyanide in Rabbit Blood. New Zealand white rabbits weighing ~4 kg were anesthetized and administered 10 mg sodium cyanide intravenously over 60 min followed by experimental treatments. Serial venous blood samples were obtained at baseline, at time of treatment, and at multiple times thereafter until 90 min following treatment. The blood was immediately cooled to 4° C., centrifuged, and the red blood cells (RBCs) were lysed in an equal volume of ice-cold water. Concentration-gradient driven collection of vapor-phase HCN following acidification of the samples with 10% trichloroacetic acid was performed in the same manner as described for both the NBA/DNB and cobinamide-based methods (Broderick, K. E.; et al. *Exp. Biol. Med.* (Maywood.) 2006, 231, 641-49).

Figure 3:
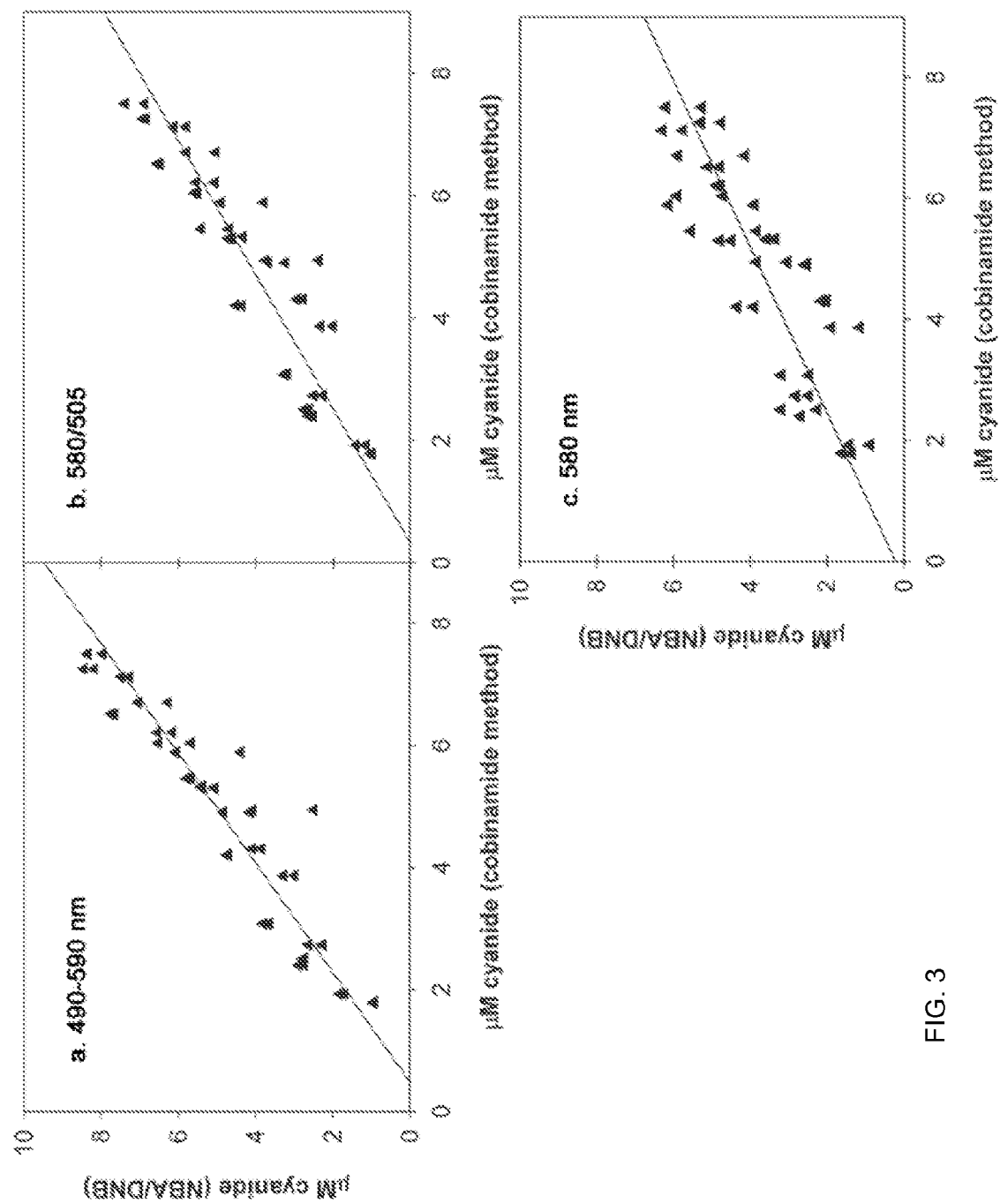
FIGS. 3a-c illustrate data from three experiments determining concentration of cyanide in rabbit blood.

The concentration of cyanide in rabbit blood was measured by both the cobinamide-based method and the NBA/DNB method. Data from three experiments are plotted in each curve of FIG. 3 revealing the correlation of these values. Concentrations of cyanide in the RBCs measured by the cobinamide-based method (x-axis) and by the NBA/DNB method (y-axis) are plotted. For the cobinamide-based method, three analyses of the data are shown: FIG. 3, panel a, 490-590 nm range analysis, FIG. 3, panel b, 580/505 ratio analysis, and FIG. 3, panel c, 580 nm single wavelength analysis. The $r^2$ of the 490-590 nm range analysis in comparison to the NBA/DNB method was 0.9 (FIG. 3, panel a), whereas it was 0.85 for the 580/505 ratio (FIG. 3, panel b), and 0.7 for the 580 nm single wavelength analysis (FIG. 3, panel c). Thus, the cobinamide-based method when applied to biological samples shows good correlation with an established method.

Figure 4:
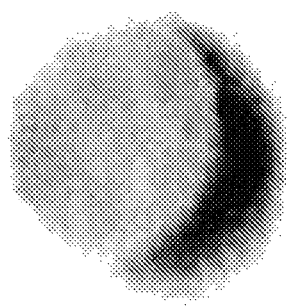
FIG. 4 illustrates filters comprising cobinamide with and without exposure to cyanide.
Figure 4:
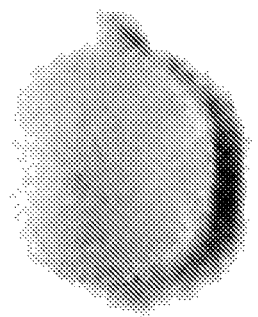

Qualitative Assay of Cyanide. A qualitative assay for cyanide was developed based on the color change that occurs when cobinamide binds cyanide. Cyanide solutions or lysed RBCs ranging in volume from 1000-1500 μl were placed in a Conway microdiffusion cell with a 1 mm diameter piece of glass fiber paper saturated with 3 μl of 80 μM dihydroxocobinamide in 0.1 M NaOH placed in the center of the interior chamber. Trichloroacetic acid (10%, 1 ml) was mixed with the fluid in the exterior chamber after sealing the cell, and color change of the filter paper was read 5 min later. The assay was as effective in rabbit blood as in cyanide standards, and could detect as little as 15 nmol of cyanide, corresponding to a cyanide concentration of ~30 μM in 0.5 ml of whole blood. FIG. 4 shows the filters. The filter on the left, which is orange in color, is from a rabbit RBC sample containing no cyanide. The filter on the right, which is pink in color, is from a rabbit RBC sample containing 15 μM cyanide, as measured by the quantitative cobinamide method.

Figure 5:
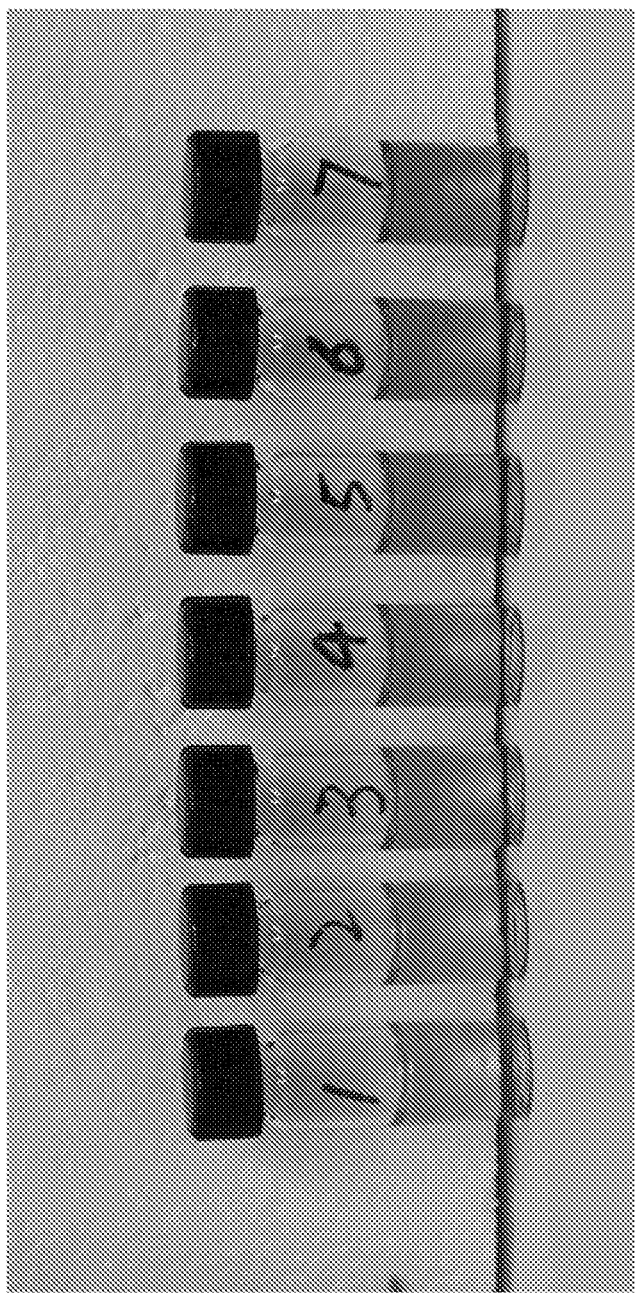
FIG. 5 illustrates the change in color of solutions of varying concentrations of cobinamide.

Additional Visual Qualitative Assay Experiment. FIG. 5 illustrates color of solutions of 50 μM cobinamide treated with increasing amounts of cyanide (0, 15, 30, 45, 60, 75 and 90 μM cyanide, from left to right) prepared in 1 mM NaOH solution at room temperature.

Figure 6:
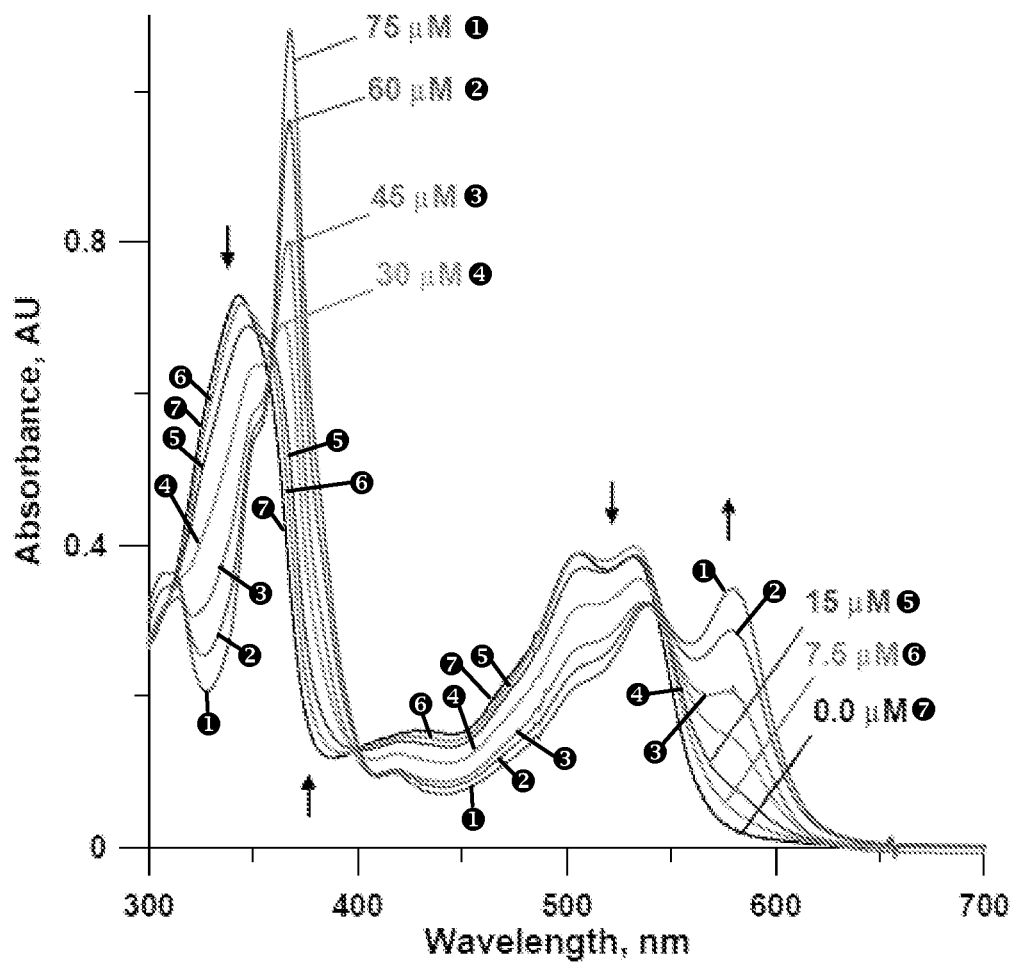
FIG. 6 illustrates spectral change in 50 µM cobinamide prepared in 60 mM NaOH upon the addition of 0-75 µM cyanide.
Figure 7:
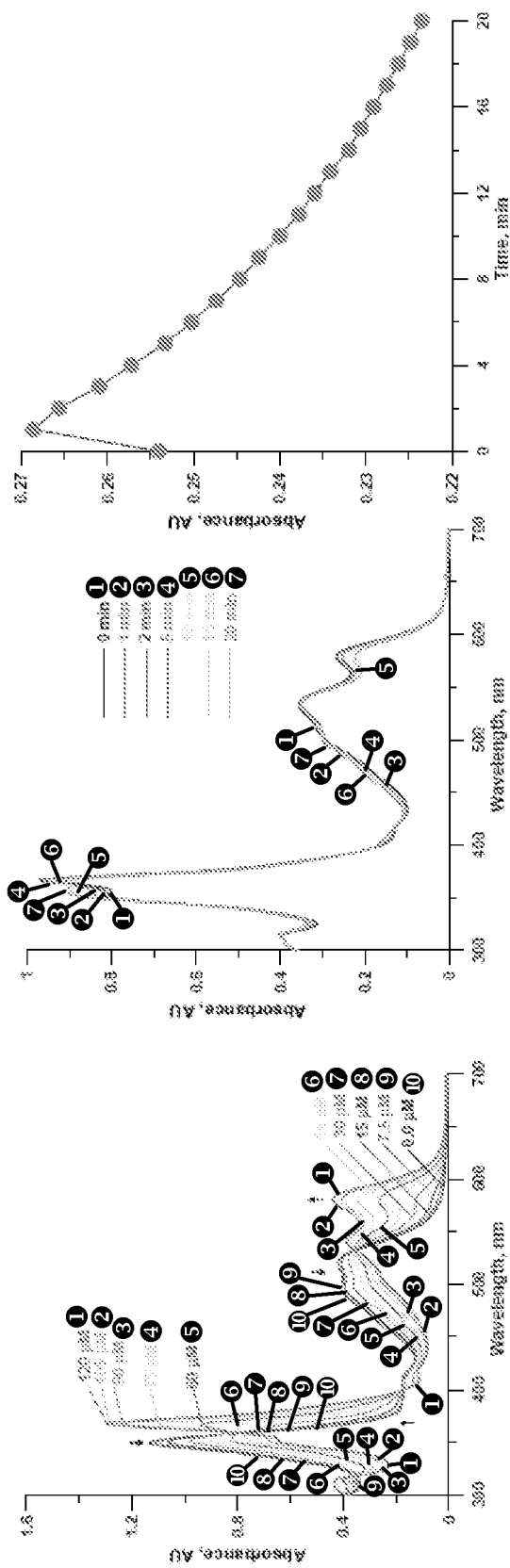
FIG. 7 are additional illustrations of spectral change in cobinamide upon addition of cyanide.
Figure 8:
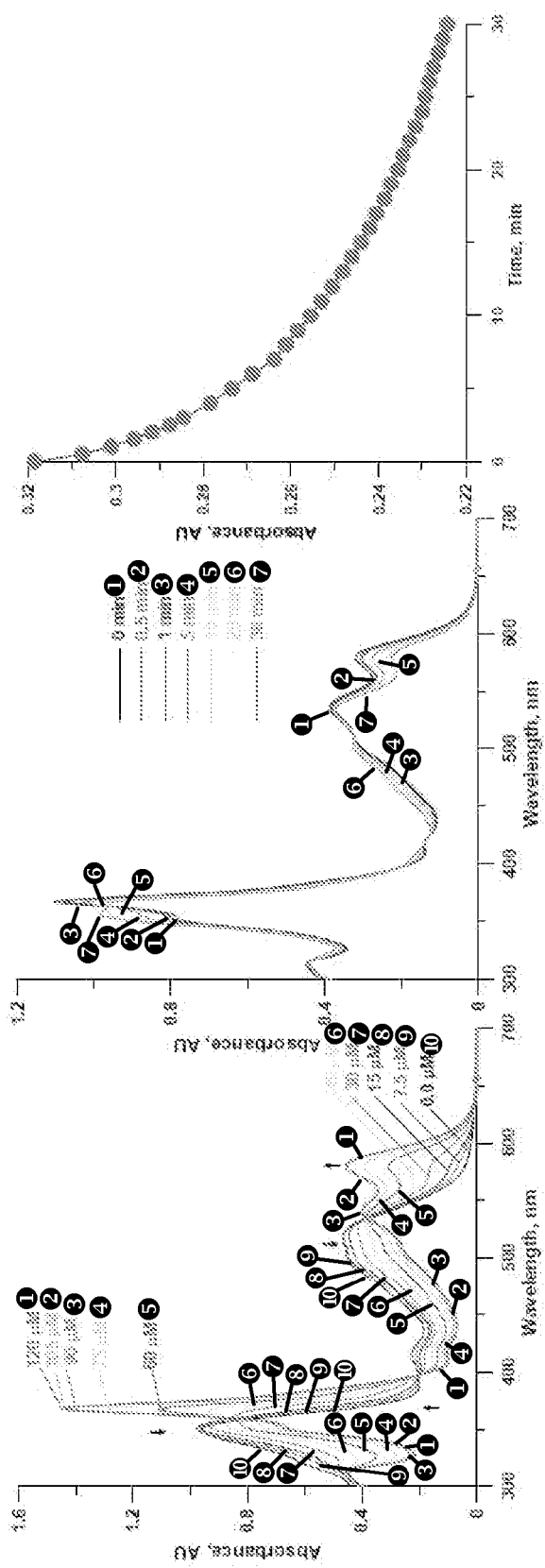
FIG. 8 are additional illustrations of spectral change in cobinamide upon addition of cyanide.
Figure 9:
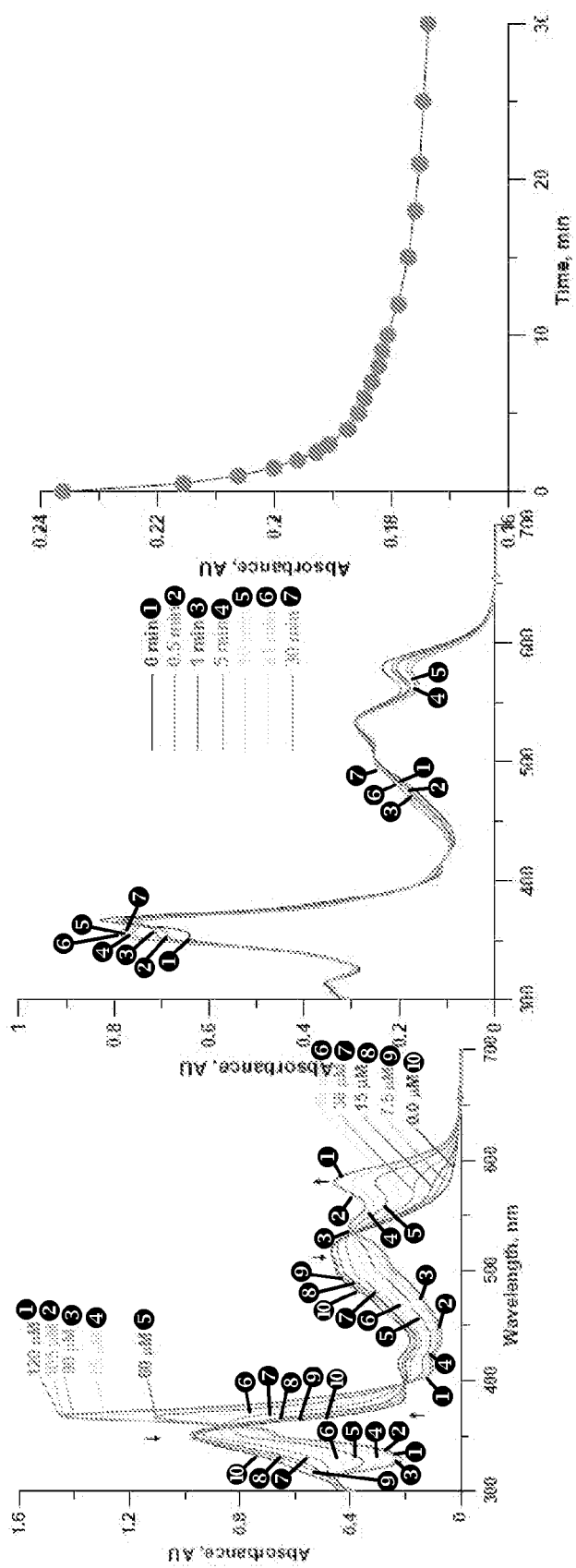
FIG. 9 are additional illustrations of spectral change in cobinamide upon addition of cyanide.

Additional Colorimetric Assay Experiment. FIG. 6 shows spectral change in 50 μM cobinamide prepared in 60 mM NaOH upon the addition of 0-75 μM cyanide. Spectra were taken 10 min. after cyanide addition. It will be observed that the bands at ~365 and 580 nm increase in absorbance upon cyanide addition while the band at ~340 nm and the pair of bands centered at ~520 nm decrease in absorbance with cyanide addition. Similar experiments were first conducted with the same concentration of cobinamide in water, in 0.1 M phosphate and borate buffer solution (each at pH 9.00). While results were similar, the final absorbance changed significantly with time. The left panel in FIG. 7 shows spectral change upon reaction with 0-120 μM cyanide; spectra taken 60 s after the reaction was initiated. The middle panel of FIG. 7 shows spectral change at different times after the reaction was initiated with 60 μM cyanide. The right panel of FIG. 7 is the same as the middle with absorbance at 580 nm as a function of time. Conditions for data shown in FIG. 8 is the same as for FIG. 7 except reaction medium was 0.1 M Na-phosphate buffer solution at pH 9.00. Conditions for data shown in FIG. 9 is the same as for FIG. 7 except reaction medium was 0.1 M Na-borate buffer solution at pH 9.00.

Figure 10:
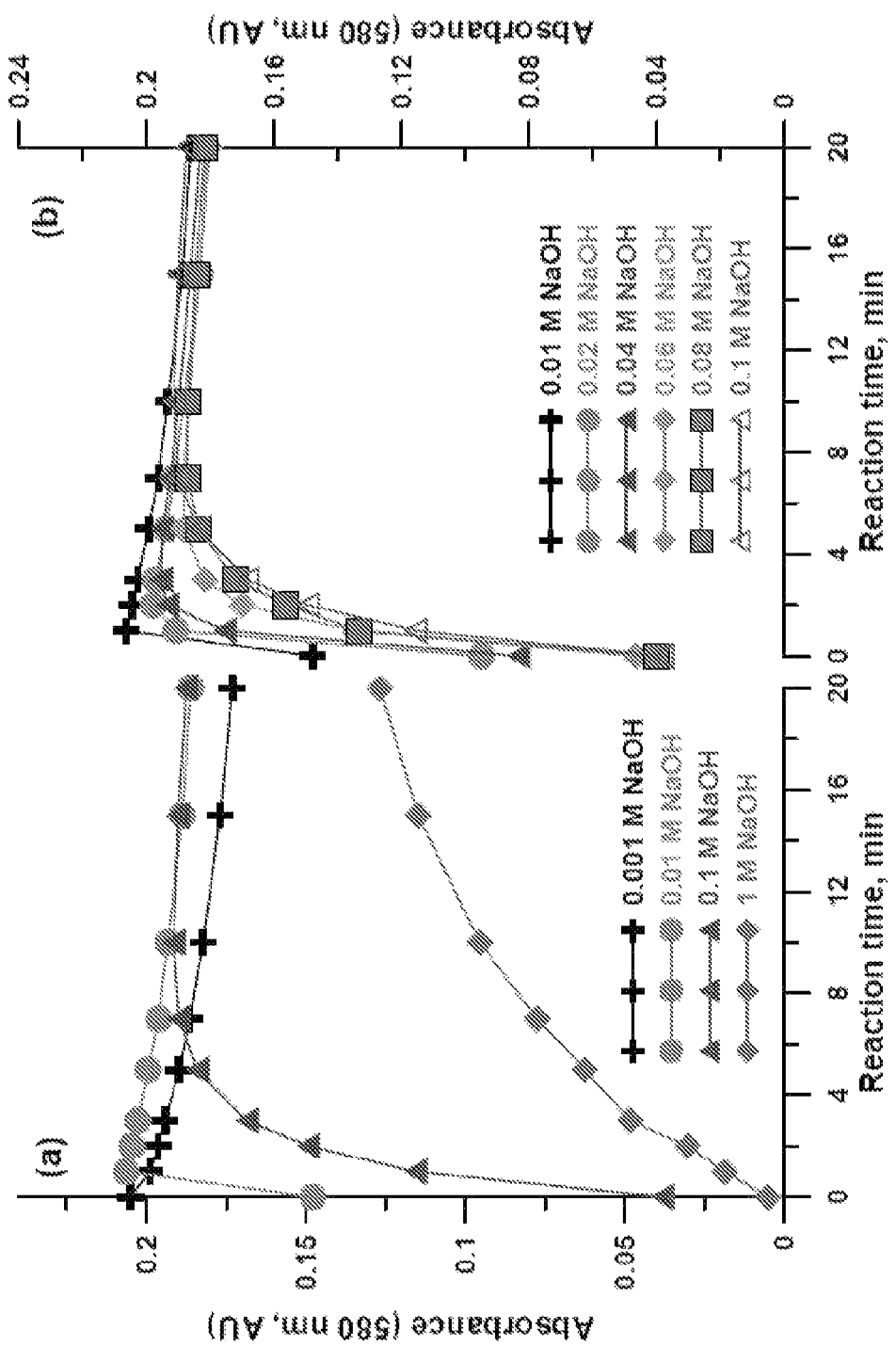
FIG. 10 illustrates absorbance change at 580 nm at different reaction times and at different pH.
Figure 11:
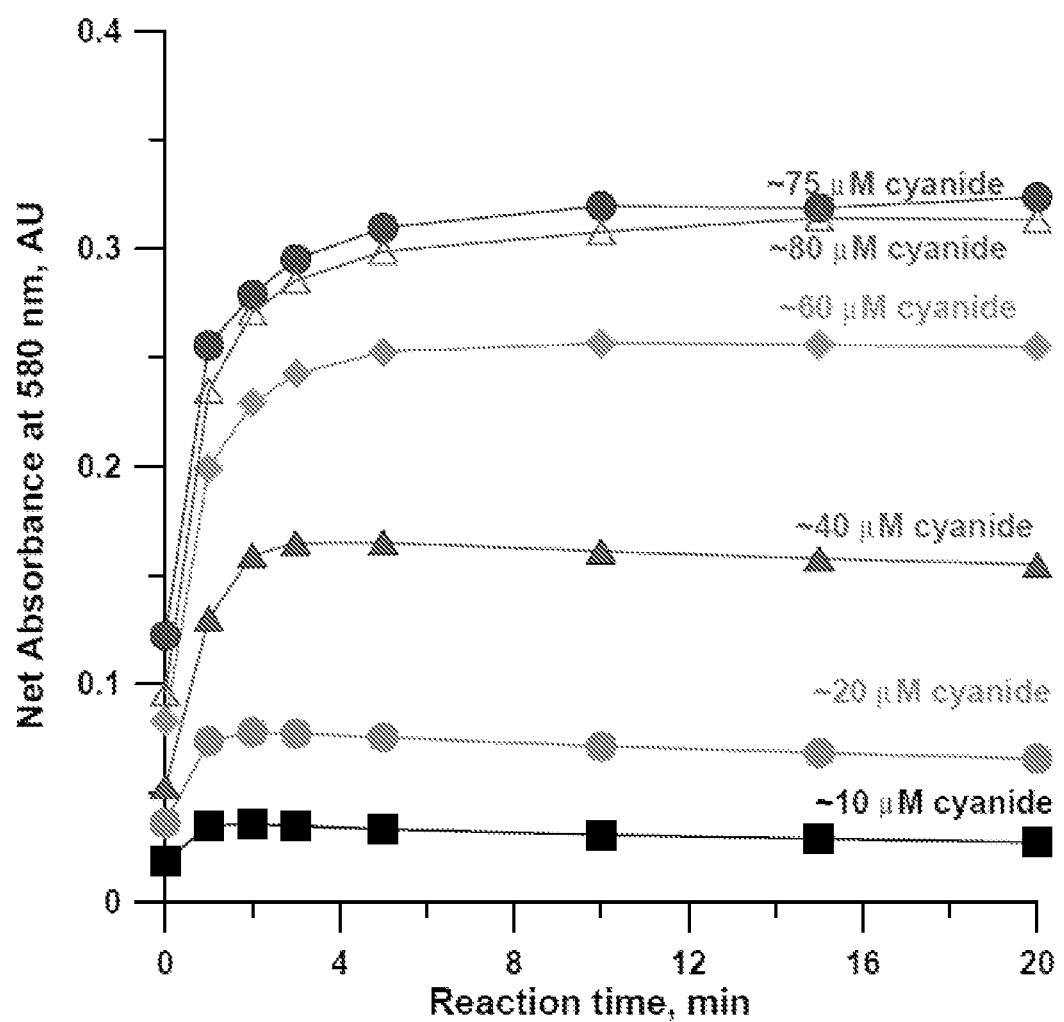
FIG. 11 illustrates temporal change in absorbance at 580 rim after 10-75 µM cyanide reacts with 50 µM cobinamide in 60 mM NaOH.

FIG. 10 shows absorbance change at 580 nm at different reaction times (60 μM cyanide reacts with 50 μM cobinamide) (a) prepared in 0.001-1 M NaOH solution, (b) prepared in 0.01-0.1 M NaOH. When cobinamide is made in an appropriate NaOH concentration, the product absorbance becomes stable after a short period. FIG. 11 shows temporal change in absorbance at 580 nm after 10-75 μM cyanide reacts with 50 μM cobinamide in 60 mM NaOH. After >~3 min, the response is reasonably stable; calibration slopes after reaction times >5 min are essentially invariant. The detailed numerical data is shown in Table 2. There was no significant improvement in the linear $r^2$ values when an intercept was allowed. Regression equations forced through zero are therefore given.

TABLE 2

Calibration curves at different reaction time

| Reaction time, min | Calibration curve (n = 6) | $r^2$ |
|---|---|---|
| 0 | Abs = (1.52 ± 0.06)*C (mM) | 0.9901 |
| 1 | Abs = (3.39 ± 0.04)*C (mM) | 0.9994 |
| 2 | Abs = (3.81 ± 0.04)*C (mM) | 0.9994 |
| 3 | Abs = (4.01 ± 0.04)*C (mM) | 0.9995 |
| 5 | Abs = (4.16 ± 0.05)*C (mM) | 0.9993 |
| 10 | Abs = (4.22 ± 0.08)*C (mM) | 0.9982 |
| 15 | Abs = (4.19 ± 0.10)*C (mM) | 0.9973 |
| 20 | Abs = (4.20 ± 0.12)*C (mM) | 0.9960 |

Figure 12:
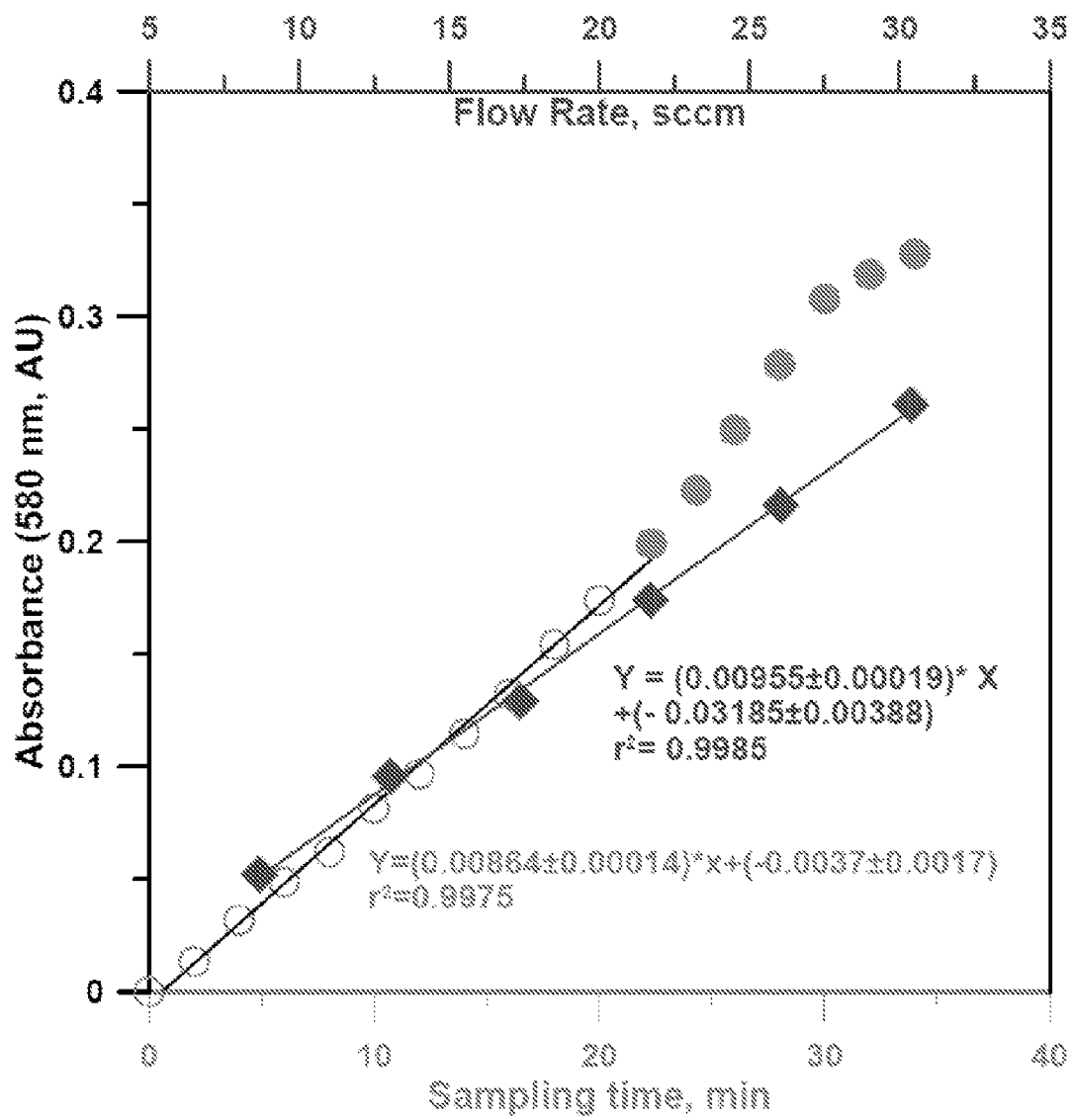
FIG. 12 illustrates absorbance change as a function of gas flow rate and sampling time.

Three "unknown" samples, nominally 20.0, 40.0 and 60.0 μM in triplicate were analyzed by the present method and by the chloramine-T/pyridinebarbituric acid standard method as described in American Public Health Association. Standard Methods for the Examination of Water and Wastewater. 21st Edition, 2005. APHA, Washington D.C. Method 4500-CN— (E: Colorimetric Method), each calibrated independently. FIG. 12 shows the result. Curve of circles: Bottom Abscissa: Absorbance change at 580 nm as a function of sampling time using 50 μM cobinamide in 60 mM NaOH as absorber. Generation solution ~0.6 mM total cyanide, 18.8° C. gas flow rate 21.7 sccm, ~25 nmol/min HCN entering absorber. Note that the slope changes after 20 min when dicyanocobinamide begins to be formed. Diamond curve: Top Abscissa: Absorbance change at 580 nm as a function of gas flow rate, 20 min sampling time, other conditions same as for curve of circles. There was no statistical difference between the analytical results at the 95% confidence level by the one tailed t-test and the correlation coefficient between the two sets of analytical results was 0.9992. In addition, with the HCN generation and capture arrangement (50 μM cobinamide in 60 mM NaOH absorber), $A_{580\,nm}$ increased linearly both with the sampling time (up to 20 min under these conditions, $r^2=0.9967$, after this the dicyano complex begins to form and the slope increases) and the flow rate (9-30 sccm, $r^2=0.9985$).

LCW Example I

Reagents. All chemicals used were reagent grade or better and 18.2 MΩ·cm Milli-Q water available from Millipore was used throughout. Pure cobinamide was produced by acid hydrolysis of cobalamin (available from Sigma-Aldrich) following Broderick et al (*J Biol. Chem.*, 2005, 280, 8678-8685). The stock cyanide solution was prepared by dissolving KCN in water and calibrated by the standard titrimetric method published by the American Public Health Association and mentioned previously herein. It was stored refrigerated. The reagent and cyanide working solution were prepared in 1 mM NaOH solution daily. The carrier was also 1 mM NaOH solution to match the matrix if not stated.

Figure 13:
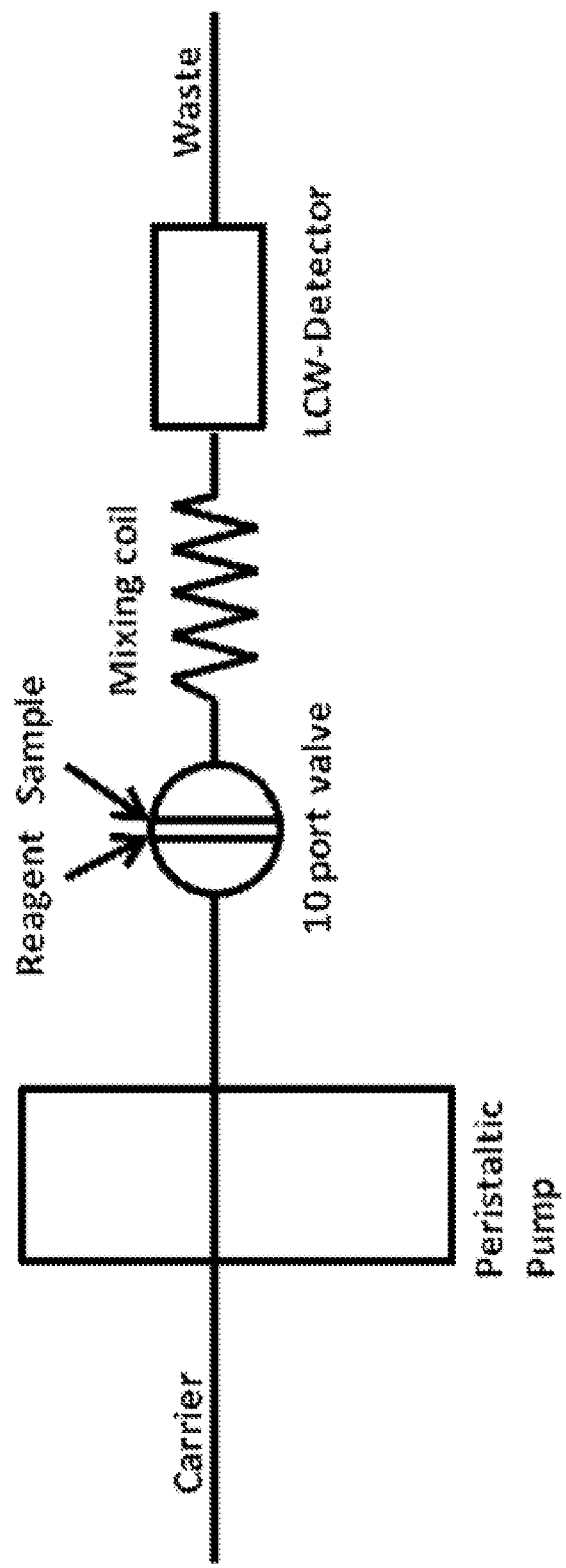
FIG. 13 illustrates the FIA-LCW analyzer according to one embodiment.

Experimental Arrangements. FIG. 13 illustrates the FIA system. It included the following parts: a Miniplus 2 peristaltic pump available from Gilson equipped with 0.040 inch i.d. PVC tubing; a 10-port electrically controlled injection valve available from Valco Instruments; a miniature USB 2000 CCD spectrophotometer available from Ocean Optics with a 600 μm i.d. fiber-optic cable, one side of which was connected to USB 2000 with s SMA-905 connector, and the other side was coupled to a ~4 cm black jacket fiber (1 mm diameter) through fit PTFE tubing. The black jacket fiber was connected to the light output of the LCW flow cell with a ¼-28 nut and a ferrule; a white LED (NSPW500BS, from Nichia Corporation), Which had useful output over the 400-700 nm range, was driven at a current of 25 mA, a 10Ω dropping resistor was used with a supply voltage of 3.8 V. The top of the LED was grinded flat until the emitter chip was ~0.5 mm from the surface and polished to optical clarity. The flat surface was directly coupled to the light input of the flow cell through a ~10 cm a black jacket fiber (1 mm diameter) using a ¼-28 nut and a ferrule. The Teflon AF-2400 tube (i.d. 0.56 mm, o.d. 0.80 mm, 500 mm in length from Biogeneral, Inc.) is located in a U-shaped curve on a black opaque acrylic sheet and sealed by another opaque acrylic sheet to protect the AF tube physically and to avoid ambient light (details see ref 66). PTFE tubing (i.d. 0.81 mm available from Zeus, Inc.) is used for making injection loop and mixing coil.

The FIA procedure was based on the sequential reagent and sample injection (100 μL) into the carrier, where cobinamide and cyanide reacted in the mixing coil. The reaction product was delivered to the LCW flow cell and detected. For cyanide detection, 583 nm, 670 nm and 531 nm were used as signal, baseline correction and blank correction wavelength, respectively. The detector output was recorded using a computer and the "counts" value (I) was converted to absorbance (A) with Excel using the equation $A=\log(I_0-I_{dark})/(I-I_{dark})$, where $I_0$ is the intensity of the light when the LCW was filled with carrier, $I_{dark}$ was detector response when the LED was turned off, I was the intensity of the light when the LCW is filled with sample. Before and after use, the LCW was sequentially flushed with pure water followed by 1 M NaOH (10 mL) and 1 M HCl (10 mL) and again with pure water (30 mL) as disclosed by Gimbert, L. J., et al. (*Trends Anal. Chem.*, 2007, 26, 914-930).

TABLE 3

Preferred parameters of the analyzer

| Parameters | Selected value |
| --- | --- |
| Detection wavelength, nm | 583 |
| Baseline correction wavelength, nm | 670 |
| Blank correction wavelength, nm | 531 |
| Data processing equation | A = A583 nm − 0.0475* A531 nm-A670 nm |
| Cobinamide concentration, μM | 10 |
| Reaction matrix, NaOH concentration, mM | 1 |
| Mixing coil length, cm | 25 |
| Flow rate, mL/min | 0.4 |
| Injection loop volume (reagent), μL | 100 |
| Injection loop volume (sample), μL | 100 |

Figure 14:
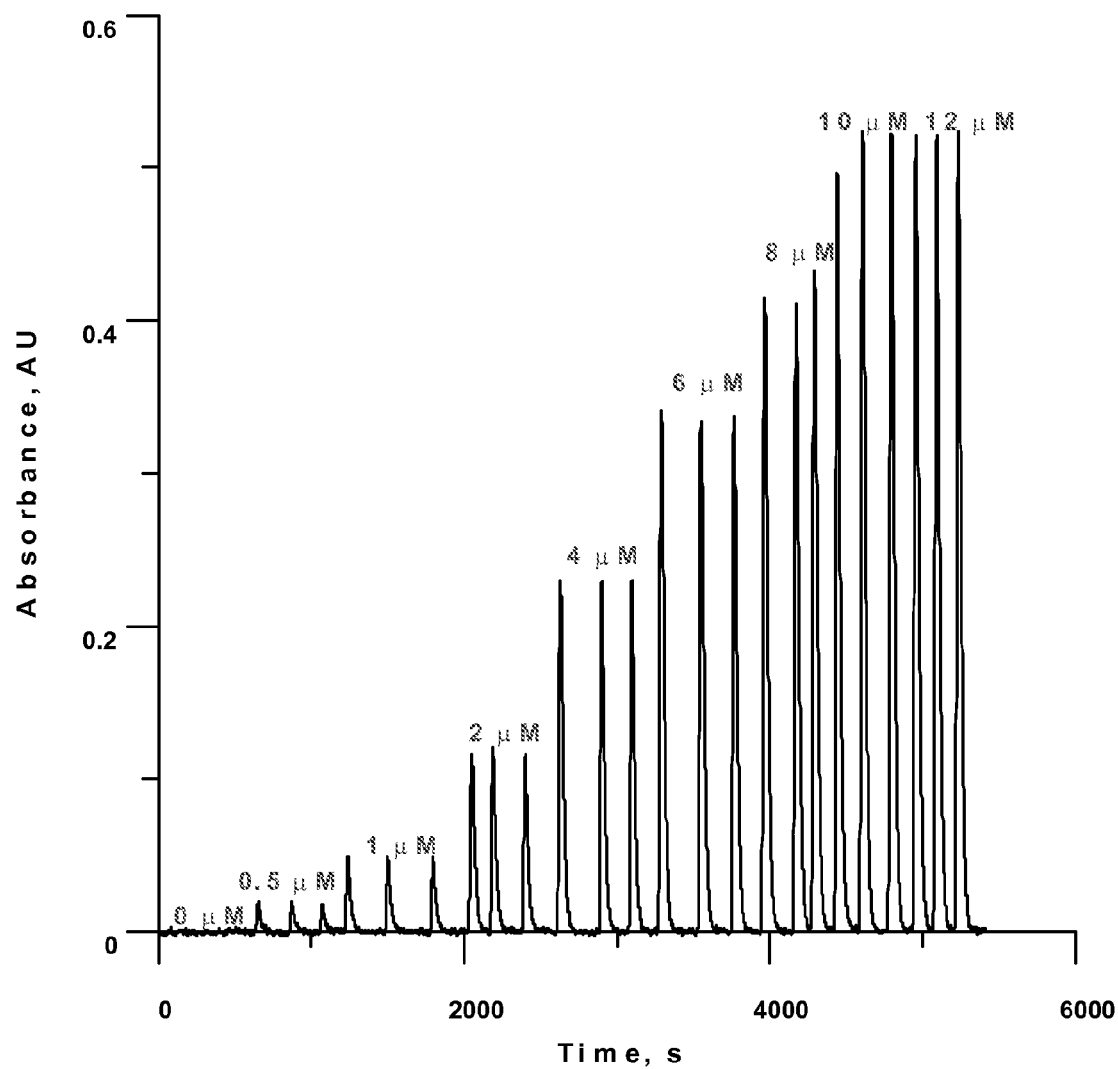
FIG. 14 illustrates a typical signal output.
Figure 15:
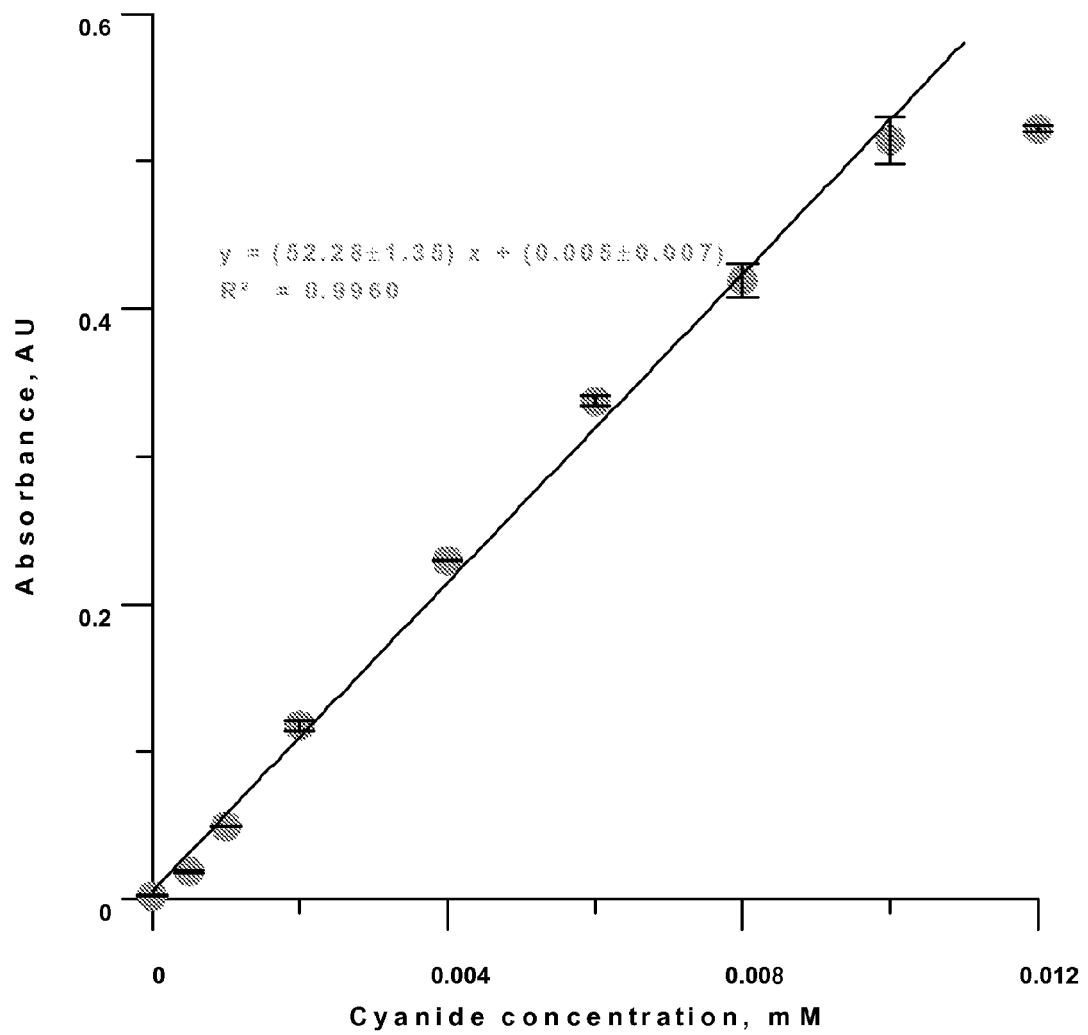
FIG. 15 illustrate a calibration curve for an analyzer according to one embodiment.

Method Validation. Table 3 summarizes the optimization of the method. Under the optimized parameters, a calibration curve was obtained over the concentration range of 0-10 μM. A typical signal output of the proposed method is shown in FIG. 14. The sample throughput can be higher than 30 h$^{-1}$. As shown in FIG. 15 (calibration curve of the analyzer), the regression equation was Abs=(52.28±1.35) $C_{CN^-}$ (mM)+ (0.005±0.007), with $R^2=0.9960$ (n=8), where Abs was the absorbance and $C_{CN^-}$ was the concentration of cyanide.

Figure 16:
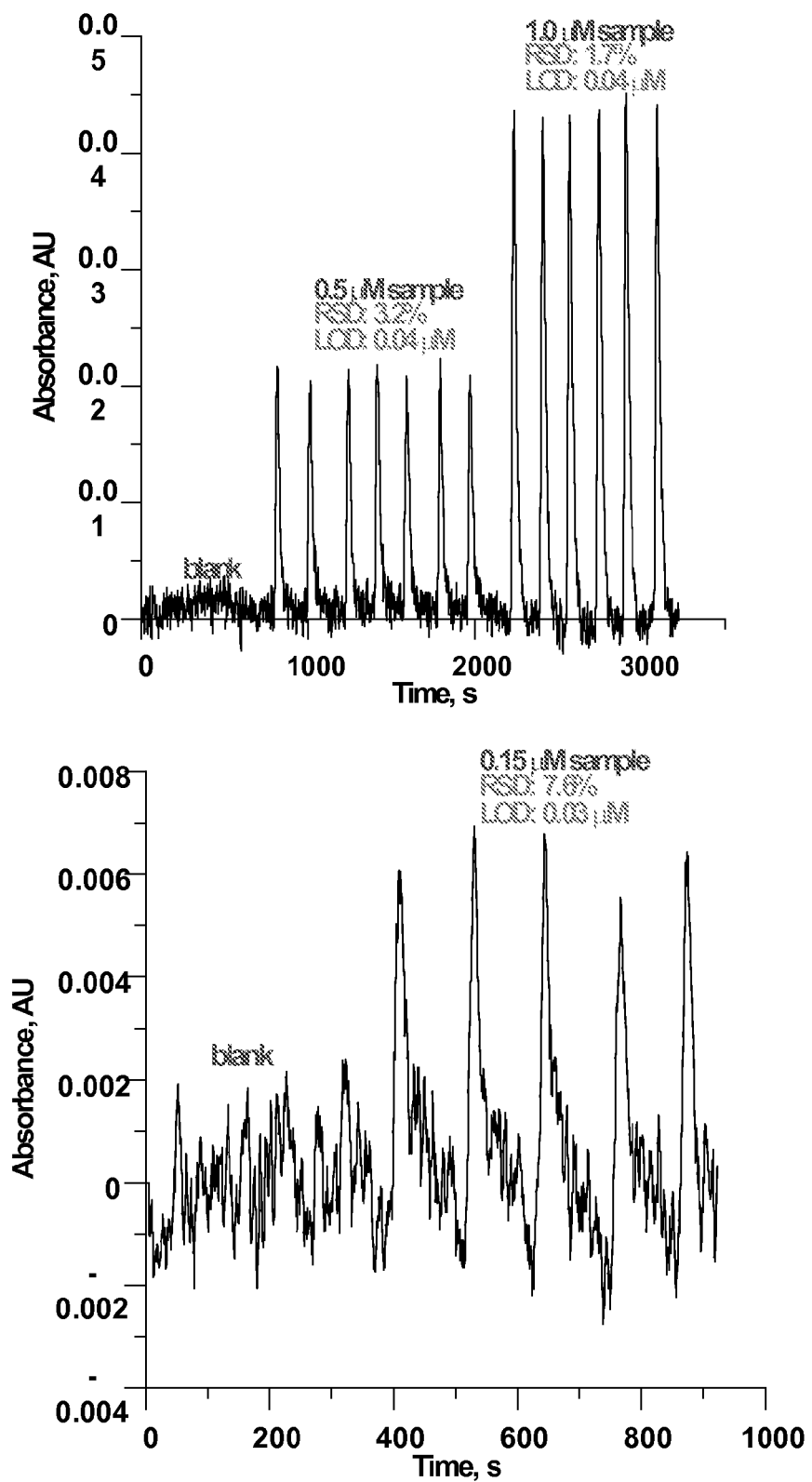
FIG. 16 illustrates that the analyzer produces reproducible analytical results at very low concentrations.

The relative standard deviations (R.S.D.) for repetitive determination of cyanide samples at 0.15, 0.5 and 1 μM, were 7.6% (n=5), 3.2% (n=7) and 1.7% (n=6), respectively. This showed good and reproducible analytical results at very low concentration (shown in FIG. 16). The RSDs were much lower than the official US, European, WHO, Australian and New Zealand standards (official standards referenced were United States Environmental Protection Agency (EPA), *Methods for chemical analysis of water and wastes*; Environmental Monitoring and Support Laboratory, Cincinnati, Ohio, 1983. http://www.epa.gov/ogwdw000/contaminants/basicinfonnation/cyanide.html. Accessed Jan. 9, 2010; Official Journal of the European Union, Commission Directive 1998/83/EC, 1998. pp. L30-42. http://eur-lex.europa.eu/LexUriServ/LexUriServ.do?uri=OJ:L:1998:330:0032:0054:EN:PDF. Accessed Jan. 9, 2010.; Official Journal of the European Union, Commission Directive 2003/40/EC, 2003. pp. L126-37. http://eur-lex.europa.eu/LexUriServ/LexUriServ.do?uri=OJ:L:2003:126:0034:0039:EN:PDF. Accessed Jan. 9, 2010.; World Health Organization. *Guidelines for drinking-water quality*, 3$^{rd}$ ed. Geneva, 2008. pp.188. http://www-.who.int/water_sanitation_health/dwq/fifftext.pdf. Accessed Jan. 9, 2010.; and Australian and New Zealand Environmental and Conservation Council (ANZECC); *Agriculture and Resource Management Council of Australia and New Zealand*. Australian Water Quality Guidelines for Fresh and Marine Water, 2000. pp. 3.4-5. http://www.mincos.gov.au/

_data/assets/pdf_file/0019/316126/wqg-ch3.pdf. Accessed Jan. 9, 2010.). Two other experiments, performed on different days, led to calibration curves of 52.06±1.19 and 52.26±1.04 AU/mM CN⁻, respectively, showing good inter-day precision and reproducibility. The LOD, estimated as 3 times the standard deviation of the measurement of low concentration samples (0.15, 0.5 and 1 μM) divided by calibration curve slope, was from 0.03 to 0.04 μM.

Figure 17:
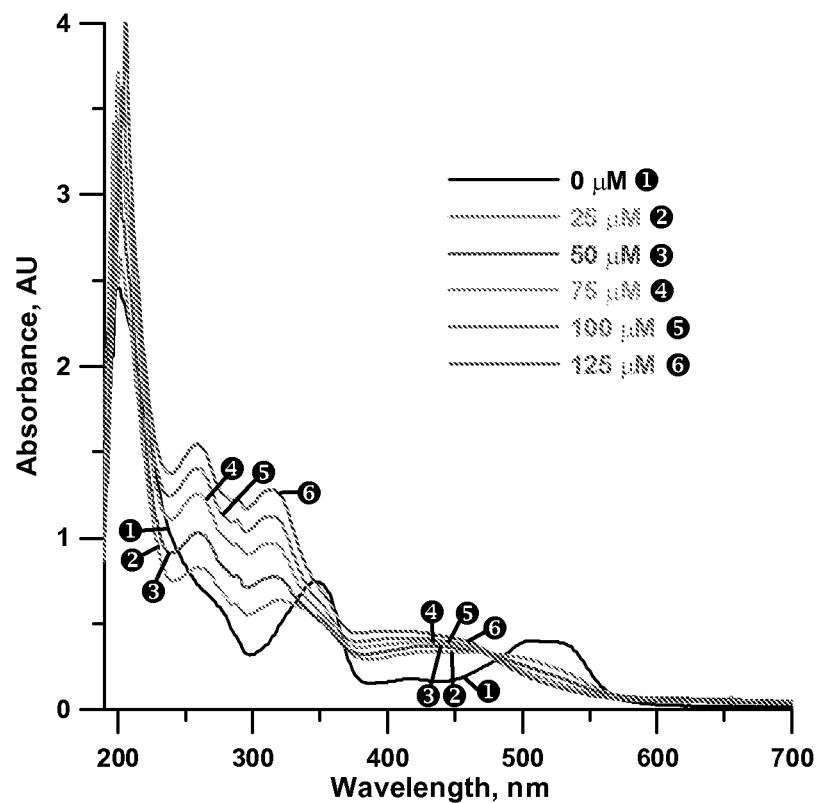
FIG. 17 illustrate the spectral change as 0-125 µM $Na_2S$ reacts with 50 µM hydroxoaquocobinamide in 1 mM NaOH solution.

Interferences. To study the selectivity of the proposed method, the effect of various species on the determination of 2 μM cyanide was tested under the optimum conditions. The tolerance limit was set as the concentration of foreign ions that produced an error ±5% in determination of cyanide. Using molar ratio, the normal ions like 50,000 fold $Na^+$ and $HCO_3^-$, 25,000 fold $H_2PO_4^-$, 1000 fold $NO_3^-$, 500 fold $Cl^-$, $K^+$, $NO_3^-$, $Br^-$, $Mg^{2+}$, $SO_4^{2-}$, $NH_4^+$, $SCN^-$, and 250 fold $SO_3^{2-}$ have no significant interference for the cyanide detection (detailed recovery data shown in Table 4). FIG. 17 shows spectral change as 0-125 μM $Na_2S$ reacts with 50 μM cobinamide in 1 mM NaOH solution. Spectra were taken immediately after reagents were mixed. It was found even 1 fold $Na_2S$ interfered. This interference problem can be solved by precipitation of sulfide by lead acetate followed by immediate filtration as disclosed by the North Carolina Division of Water Quality: *Preserving cyanide samples.* 2007. http://h2o.encstate.nc.us/lab/qa/documents/preservingcyanidesamples2.pdf. Accessed Jan. 9, 2010. and/or off-line distillation as disclosed by the United States Environmental Protection Agency (EPA), *Total and amenable cyanide (Automated colorimetric with off-line distillation). Method* 9012B. 2004. http://www.epa.gov/solidwaste/hazard/testmethods/sw846/pdfs/9012b.pdf. Accessed Jan. 9, 2010.

TABLE 4

Interference of common ions on the determination of 2 μM cyanide

| Interference ions | Recovery, % (n = 3) |
|---|---|
| 100 mM NaHCO₃ | 102.7 ± 1.0 |
| 50 mM NaH₂PO₄ | 104.1 ± 2.8 |
| 1 mM NaCl | 97.3 ± 2.7 |
| 1 mM Ca(NO₃)₂ | 97.0 ± 3.8 |
| 1 mM KCl | 95.2 ± 0.8 |
| 1 mM NaNO₃ | 104.8 ± 4.8 |
| 1 mM NaBr | 104.2 ± 2.34 |
| 1 mM MgSO₄ | 101.9 ± 3.2 |
| 100 μM NH₄Cl | 102.2 ± 3.8 |
| 1 mM NH₄Cl | 98.5 ± 3.1 |
| 2 mM NH₄Cl | 70.4 ± 2.7 |
| 10 μM Na₂SO₃ | 99.5 ± 1.4 |
| 100 μM Na₂SO₃ | 97.8 ± 5.0 |
| 500 μM Na₂SO₃ | 96.7 ± 3.0 |
| 1 mM Na₂SO₃ | 57.5 ± 6.9 |
| 10 μM KSCN | 99.3 ± 3.7 |
| 100 μM KSCN | 98.9 ± 1.2 |
| 1 mM KSCN | 103.2 ± 1.1 |
| 2 mM KSCN | 116.1 ± 2.08 |
| 2 μM Na₂S | 122.5 ± 7.1 |
| 5 μM Na₂S | 127.2 ± 5.8 |
| 10 μM Na₂S | 148.0 ± 8.2 |
| 20 μM Na₂S | 158.1 ± 7.4 |
| 100 μM Na₂S | 188.1 ± 12.2 |
| 1 mM Na₂S | 253.7 ± 14.9 |

Analysis of Fruit Seeds. Commercially available fruit was purchased from a local market. The seeds were removed from the fruit and put in 10 mL pre-weighted vial and then weighed to get the net weight of seeds. After addition of 5 mL 1 mM NaOH solution as washing solution, the vial was capped and shaken for 1 min. Then the washing solution was filtered using an on-line 0.45 μm nylon filter, and 1.5 mL was analyzed and the other 3 mL was spiked with 1 and 2 μM cyanide and then determined using the analyzer. The seeds were washed, mixed with new washing solution, filtered, spiked and analyzed again. The procedure was repeated until no detectable cyanide was found. All the samples were analyzed in triplicate.

The experimental results are tabulated in Table 5. No cyanide was detected in the orange sample, while the apple and pear seeds had detectable cyanide. However, after 4 times washing, there was no detectable cyanide in washing solution for apple and pear seeds. Männel-Croisé, et al. showed washing could be an efficient way to remove hydrogen cyanide in biological samples (*Anal. Chem.*, 2009, 81, 9493-9498). The accuracy of the proposed method was evaluated by recovery experiments after spiking the washing solution at 1 and 2 μM. Percent recoveries, which are shown in Table 5, were acceptable in all cases, ranging between 91.5-107.9%.

TABLE 5

Fruit seeds samples and recoveries in washing solution

| | concentration in washing solution | | | seed | concentration |
|---|---|---|---|---|---|
| Fruit | added, μM | found, μM | Recovery, % | weight, g | in fruit, μg/g |
| Apple seed, 1st wash | 0 | 0.47 ± 0.07 | | | 0.178 ± 0.025 |
| | 1 | 1.47 ± 0.03 | 99.7 ± 3.4 | | |
| | 2 | 2.61 ± 0.05 | 106.9 ± 2.6 | | |
| Apple seed, 2nd wash | 0 | 0.18 ± 0.03 | | | 0.068 ± 0.010 |
| | 1 | 1.17 ± 0.09 | 98.5 ± 9.0 | | |
| | 2 | 2.61 ± 0.05 | 105.5 ± 5.4 | | |
| Apple seed, 3rd wash | 0 | 0.06 ± 0.01 | | | 0.025 ± 0.004 |
| | 1 | 1.07 ± 0.07 | 100.9 ± 7.2 | | |
| | 2 | 2.19 ± 0.02 | 106.1 ± 1.3 | | |
| Apple seed, 4th wash | 0 | N.D. | | | N.D. |
| | 1 | 1.01 ± 0.03 | 101.1 ± 3.5 | | |
| | 2 | 2.07 ± 0.09 | 103.6 ± 4.7 | | |
| Apple seed, total | | | | 0.34693 | 0.271 ± 0.039 |
| Pear seed, 1st wash | 0 | 0.76 ± 0.04 | | | 0.406 ± 0.020 |
| | 1 | 1.72 ± 0.08 | 96.4 ± 7.9 | | |
| | 2 | 2.93 ± 0.05 | 108.5 ± 2.7 | | |
| Pear seed, 2nd wash | 0 | 0.48 ± 0.03 | | | 0.256 ± 0.014 |
| | 1 | 1.39 ± 0.06 | 91.5 ± 6.3 | | |
| | 2 | 2.64 ± 0.09 | 107.9 ± 4.6 | | |
| Pear seed, 3rd wash | 0 | 0.13 ± 0.02 | | | 0.067 ± 0.008 |
| | 1 | 1.07 ± 0.02 | 100.9 ± 7.2 | | |
| | 2 | 2.26 ± 0.11 | 106.1 ± 1.3 | | |
| Pear seed, 4th wash | 0 | N.D. | | | N.D. |
| | 1 | 0.96 ± 0.06 | 95.5 ± 6.3 | | |
| | 2 | 2.09 ± 0.07 | 104.5 ± 3.7 | | |
| Pear seed, total | | | | 0.24215 | 0.729 ± 0.042 |
| Orange seed, 1st wash | 0 | N.D. | | 0.18076 | N.D. |
| | 1 | 0.93 ± 0.01 | 93.3 ± 1.3 | | |
| | 2 | 2.17 ± 0.09 | 105.8 ± 4.7 | | |

Analysis of Breath Air Samples. Samples were taken from 3 volunteers (1 woman and 2 men) aged 28-35 years. No special inclusion criteria were required. Two samples were collected from each volunteer—the first and second samples taken at different times. A sample of mixed exhaled air was directly collected by two serial 30-mL capacity, fitted, midget bubblers using 10 mL 1 mM NaOH as absorber. The quantitative collection of cyanide by the upstream bubbler was verified by cyanide detection results in the contents of the downstream bubbler. The exit of the second bubbler was connected to a mass flow controller (MFC, UFC01100A) via a water trap bottle to protect the MFC. The output signal (V, voltage) of the MFC display panel was recorded in real time by a computer with a USB-based data acquisition board (DAQ) USB-1408FS available from Measurement Computing. The actual flow rate was first measured by a Primary Flow Calibrator available from Gilian Instrument Co and calibrated to standard cubic centimeter per minute (sccm). The flow rate (sccm)=(3021±15) *V+(−620±7), $r^2$=0.9998 (n=11). The total volume of the sample was integrated by the flow rate and sampling time. After sample collection, ~4 mL of the concentrated sample was injected into the FIA system after filtration with a 0.45 μm nylon filter and determined; another 5 mL sample was spiked with 1 μM cyanide solution and determined after filtration. The amount of HCN was calculated to standard volume (standard liter), which is divided by the total sample volume (standard liter) to get the concentration (ppbv) in breath air. All the samples were analyzed in triplicate.

CAUTION. Cyanide is extremely toxic and hazardous HCN is easily evolved. Care must be taken to avoid skin contact and inhalation/ingestion. The entire experimental setup was located in a well-ventilated hood. Gaseous HCN generated in the experiments was trapped in a bubbler containing alkaline hypochlorite (5% bleach solution containing added alkali) before disposal. Comparable measures should be taken if similar experiments are performed as reported by Whiteman, D. A., et al. (*Anal. Chem.,* 1991, 63, 775-781).

The experimental results are tabulated in Table 6. The detected HCN concentration was in accordance with the published value, which was from 0 to 62 ppbv (Stamyr, K., et al. *Biomarkers,* 2009, 14, 285-291; Lundquist, P., et al. *Arch. Toxicol.,* 1988, 61, 270-274; Španel, P., et al. *J. Breath Res.,* 2007, 1, 026001-8; Španel, P., et al. *J. Breath Res.,* 2007, 1, 011001-4; and Wang, T., et al. *J. Breath Res.,* 2008, 1, 037013-25). The accuracy of the proposed method was evaluated by recovery experiments after spiking the absorbing solution at 1 μM. Percent recoveries shown in Table 6 were acceptable in all cases, ranging between 91.2-104.8%. It should be noted there was no detected HCN in the second bubbler, indicating a high capture efficiency of the first bubbler.

TABLE 6

Breath air samples and recoveries in absorbing solution

| Sample | concentration in absorbing solution | | | sample volume, SL | concentration in breath air, pbv |
|---|---|---|---|---|---|
| | added, μM | found, μM | Recovery, % | | |
| 1-bubbler 1 | 0 | 0.070 ± 0.007 | | 0.641 | 24.4 ± 2.61 |
| | 1 | 1.081 ± 0.035 | 101.1 ± 3.5 | | |
| 1-bubbler 2 | 0 | N.D. | | | |
| | 1 | 0.937 ± 0.011 | 93.7 ± 1.1 | | |
| 2-bubbler 1 | 0 | 0.125 ± 0.009 | | 1.709 | 16.3 ± 1.2 |
| | 1 | 1.146 ± 0.047 | 102.1 ± 4.7 | | |
| 2-bubbler 2 | 0 | N.D. | | | |
| | 1 | 0.912 ± 0.010 | 92.1 ± 1.0 | | |
| 3-bubbler 1 | 0 | 0.373 ± 0.014 | | 2.362 | 35.4 ± 1.4 |
| | 1 | 1.377 ± 0.030 | 100.4 ± 3.0 | | |
| 3-bubbler 2 | 0 | N.D. | | | |
| | 1 | 0.959 ± 0.015 | 95.9 ± 1.5 | | |
| 4-bubbler 1 | 0 | N.D. | | 1.139 | N.D. |
| | 1 | 1.048 ± 0.019 | 104.8 ± 1.9 | | |
| 4-bubbler 2 | 0 | N.D. | | | |
| | 1 | 0.920 ± 0.042 | 92.0 ± 4.2 | | |

LCW Examples II

Using Aquocyanocobinamide

Reagents—All chemicals used were reagent grade or better and 18.2 MΩ·cm Milli-Q water available from Millipore was used throughout. Pure aquocyanocobinamide was synthesized according to Männel-Croisé and Zelder (*Inorg. Chem.* 2009, 48, 1272-1274). Pure hydroxoaquocobinamide was produced by acid hydrolysis of cobalamin (available from Sigma-Aldrich) following Broderick et al (*J Biol. Chem.,* 2005, 280, 8678-8685). The stock cyanide solution was prepared by dissolving KCN in water and calibrated by the standard titrimetric method published by the American Public Health Association and mentioned previously herein and stored refrigerated. The carrier solution was 100 mM carbonate buffer solution (pH 10.44). The reagent and cyanide working solutions were prepared in carrier solution daily except as stated.

Figure 18:
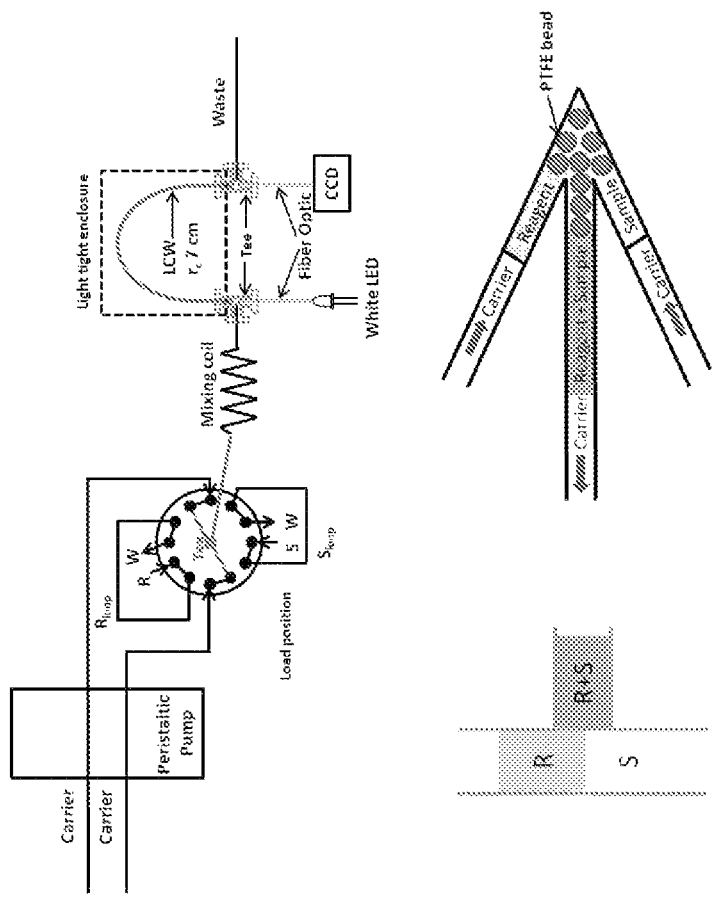
FIG. 18 illustrates an FIA-LCW analyzer according to one embodiment.

Experimental Arrangements. The experimental system is shown in FIG. 18 and is similar to that in FIG. 13, except that the peristaltic pump was equipped with two tubings instead of one and a 12-port electrically controlled injection valve with PEAK wetted parts (available from Valco Instruments) instead of the previous 10-port valve. Therefore this merging zone manifold replaced the penetration zone design. PTFE tubing (i.d. 0.86 mm, 1.68 mm o.d., 20 SW or i.d. 0.46 mm, 0.92 mm o.d., 26 SW from Zues Inc.) was used as fluid conduits throughout. The bottom images in FIG. 18 show the reagent mixer with the sample (left: a commercial Tee for mixing; right, arrow mixer with PTFE beads for better mixing).

The system injects 160 μL of sample and reagent individually into the carbonate buffer carrier, the two zones merge and mix in the mixer (commercial Tee available from Upchurch Scientific or lab-made arrow mixer filled with 1.5 mm i.d. PTFE beads), the mixing coil (MC) and the LCW cell ($V_{cell}$=123 μL) where it is detected. Integration of 588, 589, 590, 591, 592 nm output (counts) for signal and 670 nm values for drift correction respectively were used. The calculation of absorbance from counts is as described for LCW Example I. In the primary experiment, the 583 nm absorbance was used as signal for parameter optimization. The LCW was flushed with pure water, 1 M NaOH (10 mL) and 1 M HCl (10 mL) and finally again with pure water (30 mL) prior to use and storage.

Figure 19:
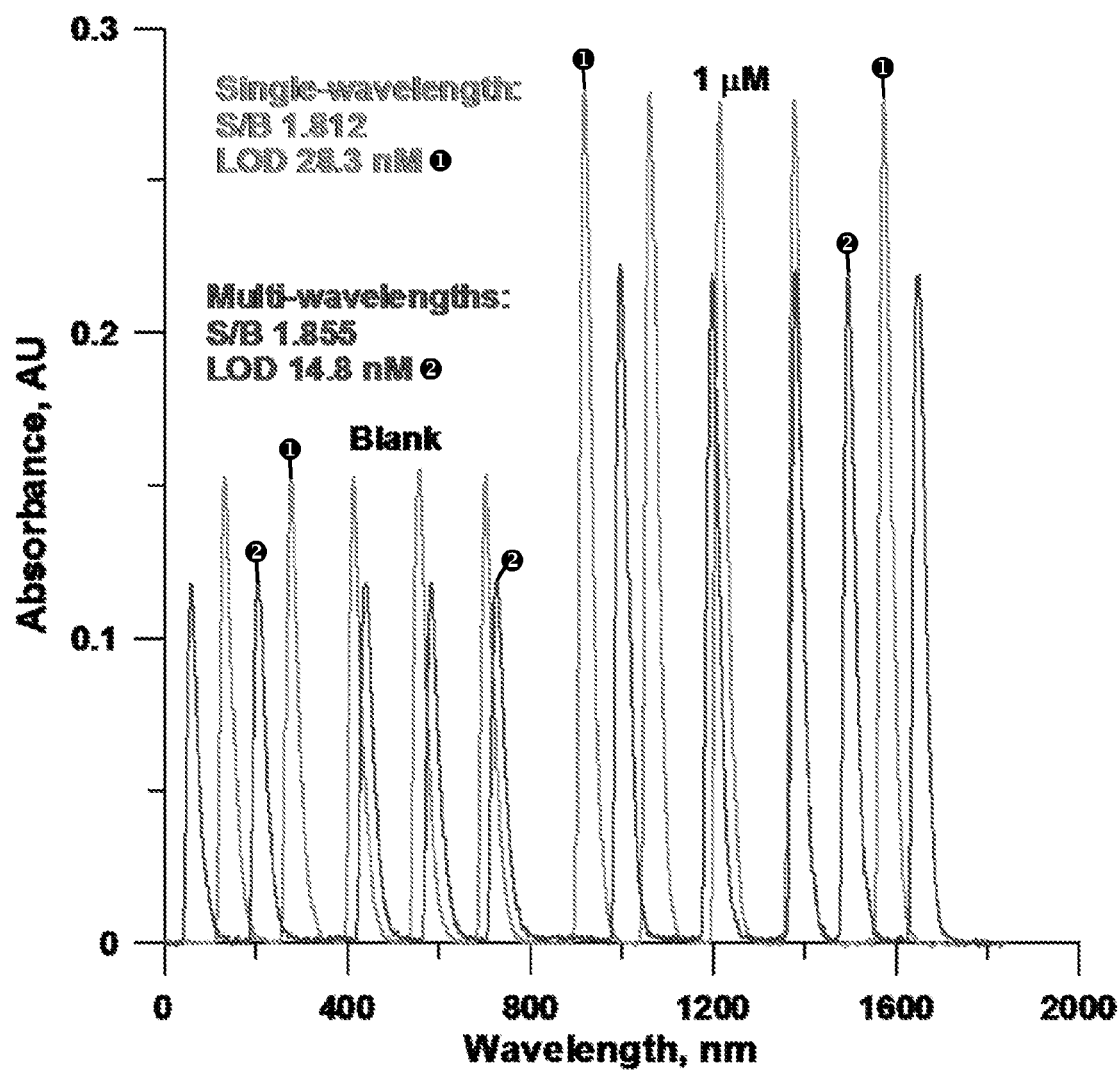
FIG. 19 illustrates that integration of multiple wavelengths reduced the noise to get better signal to noise ratio (S/N), which gave a lower limit of detection (LOD).

Due to absorbance of cobinamides by Teflon AF used in the analyzer, a correction formula was applied for compensation of the baseline shift and the reagent blank response using Microsoft Excel Solver™ to find the best fit correction coefficients. If significant levels of interfering compounds (e.g. sulfide) are present in the sample, the reagent blank correction based on the isosbestic point is not optimal. Here 670 nm absorbance is chosen for base line shift or Schlieren effects correction, but the detection wavelength is the integration of multi-wavelengths 588, 589, 590, 591 and 592 nm to give a better signal to blank ratio (S/B). Though the absolute absorbance of ~590 nm is lower than 583 nm, this multi-wavelength integration reduced the noise leading to improved S/N, which gave a lower LOD as shown in FIG. 19.

Figure 20:
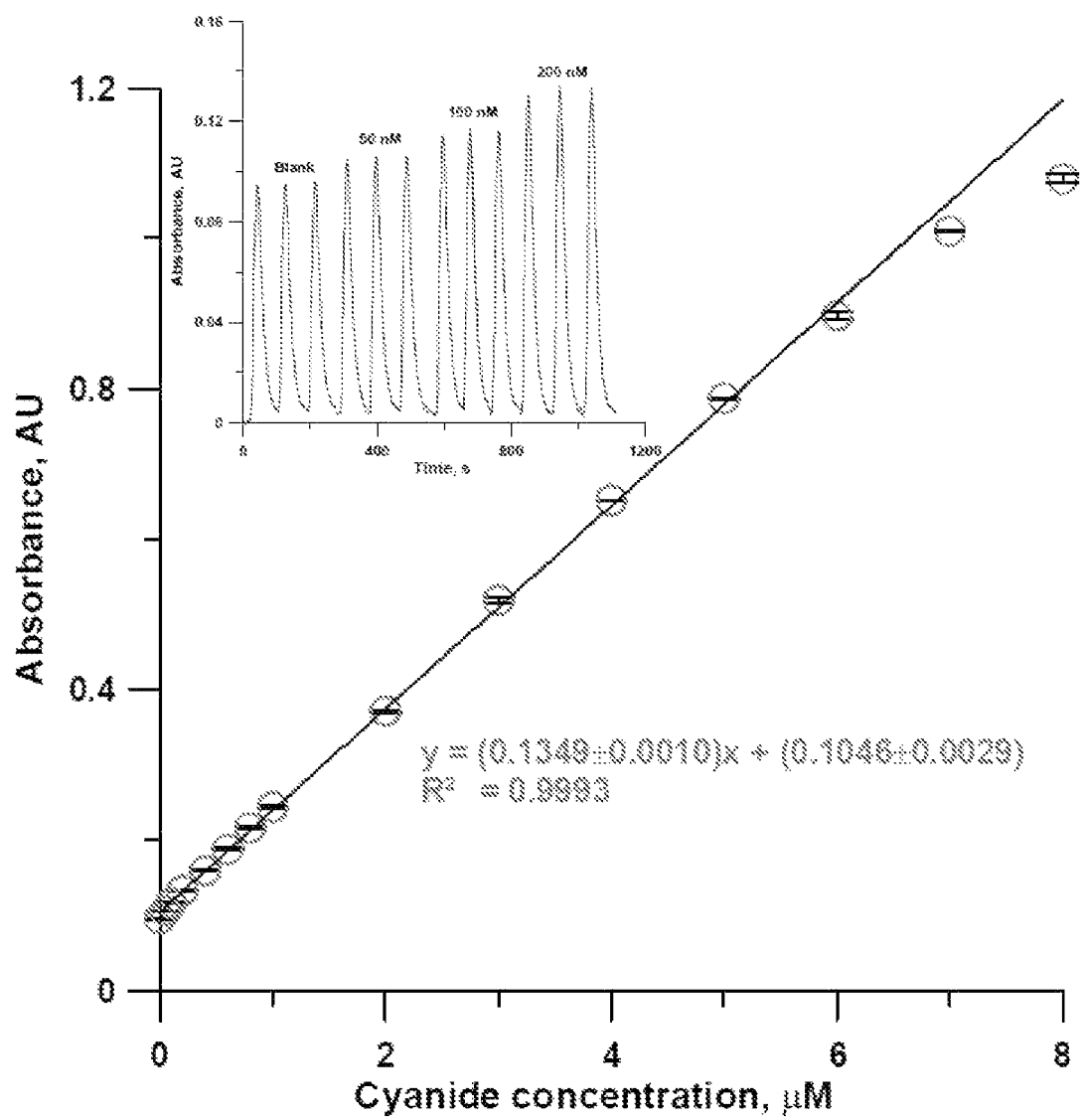
FIG. 20 illustrates a calibration curve for an analyzer according to one embodiment.
Figure 20A:
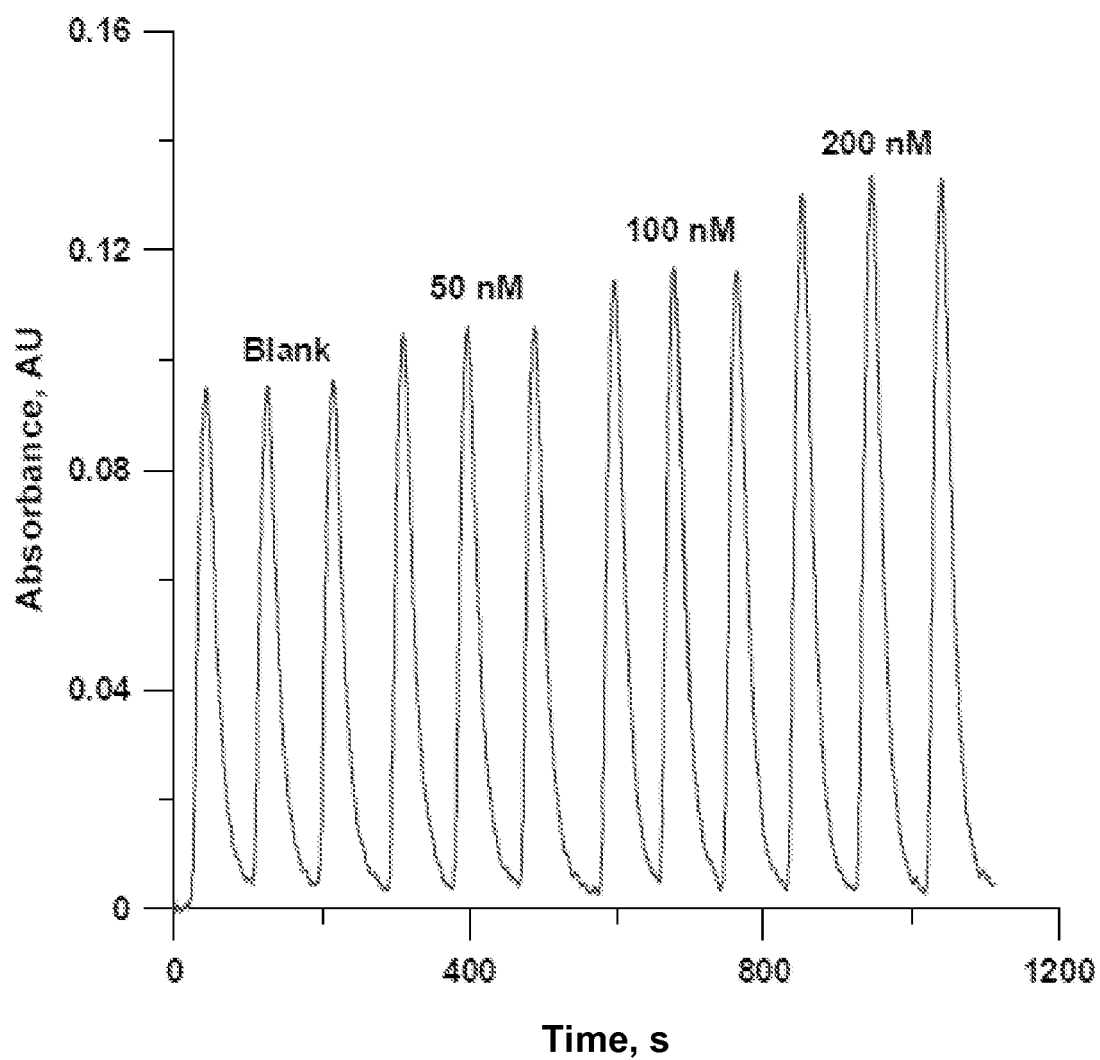
FIG. 20a illustrates the response of the analyzer according to one embodiment.

Using a 160 μL sample/reagent loop, an arrow mixer, flow rate 0.4 mL/min, 75 cm 0.46 mm i.d. SS2 design MC, detector 500 mm×0.56 mm i.d. LCW, 10 μM aquocyanocobinamide and multi-wavelength detection, response of the system to 0, 50, 100 and 200 nM cyanide was studied. FIG. 20 shows the resulting calibration curve. Error bars indicate ±1 S.D. (n=3). The calibration curve is linear up to 6 μM. The response deviated from Beer's Law at higher concentrations (high absorbance value). The maximum sampling frequency (with <1% carryover) is 40 samples/h. The response at 0, 50, 100 and 200 nM CN⁻ are shown in the inset of FIG. 20, FIG. 20*a*. The relative standard deviation of 50 and 100 nM samples were 0.49% (n=5) and 1.07% (n=5), respectively. The LOD estimated from three times the standard deviation of the blank samples divided by the calibration slope is only 8 nM.

Analysis of Fruit Seeds. The fruit seed sample treatment is as described in detail in LCW Example I. The hydrolytically obtained cyanide content of the tested fruit seeds were 1.75±0.02, 1.30±0.02 and 1.03±0.06 mg/kg for apple seeds; 14.7±0.08, 6.78±0.22 and 9.22±0.46 mg/kg for peach seeds; 8.55±0.37, 6.60±0.16 and 6.24±0.14 mg/kg for almond seeds, respectively (the standard deviation reflects the analytical uncertainty in repeat analysis of the same extract, not variation between seed samples). In separate experiments, 1 µM spike recoveries ranged between 94.7-104.3%.

Analysis of Saliva Samples. Sample donors were in all in good health at time of sampling. The unstimulated saliva samples were collected directly into 15 mL polypropylene centrifuge tubes. 10 mL 100 mM carbonate buffer (pH 10.44) was added immediately for dilution and matching to the analysis system matrix. The samples were kept in 4° C. and filtered with 1.2 µm nylon syringe filters before analysis. All the samples were analyzed within 2 h. The same experimental setup except for a ~20 cm LCW was also utilized for thiocyanate analysis based on its reaction with Fe (III) in acid medium. The same saliva samples for cyanide analysis were adjusted with 5% (v/v) $HNO_3$ before analysis to match the analysis system matrix.

For smoking effect experiment, an occasional and a heavy smoker were recruited. Before smoking, they were asked to give a saliva sample as background value. After smoking a cigarette with inhalation like most smokers, saliva samples were collected again at multiple times after the smoking and treated for cyanide and thiocyanate analysis as described above.

Salivary cyanide concentrations of non-smokers measured here were, respectively: 3.95±0.12, 4.54±0.14, 4.79±0.15, 3.92±0.01 and 6.07±0.57 µM. Percent recoveries ranged from 91.1-104.3%. (Details of standard addition are given Table S2). The saliva sample storage condition and the most likely interfering analyte, thiocyanate, were also evaluated. 1 µM spiked diluted saliva sample could be stored in 4° C. for at least 3 h while in room temperature, the max storage time is ~2 h. Referring to molar ratios, 5000×$SCN^-$ resulted in <±5% error in the determination of 0.2 µM $CN^-$ in diluted saliva.

Figure 21:
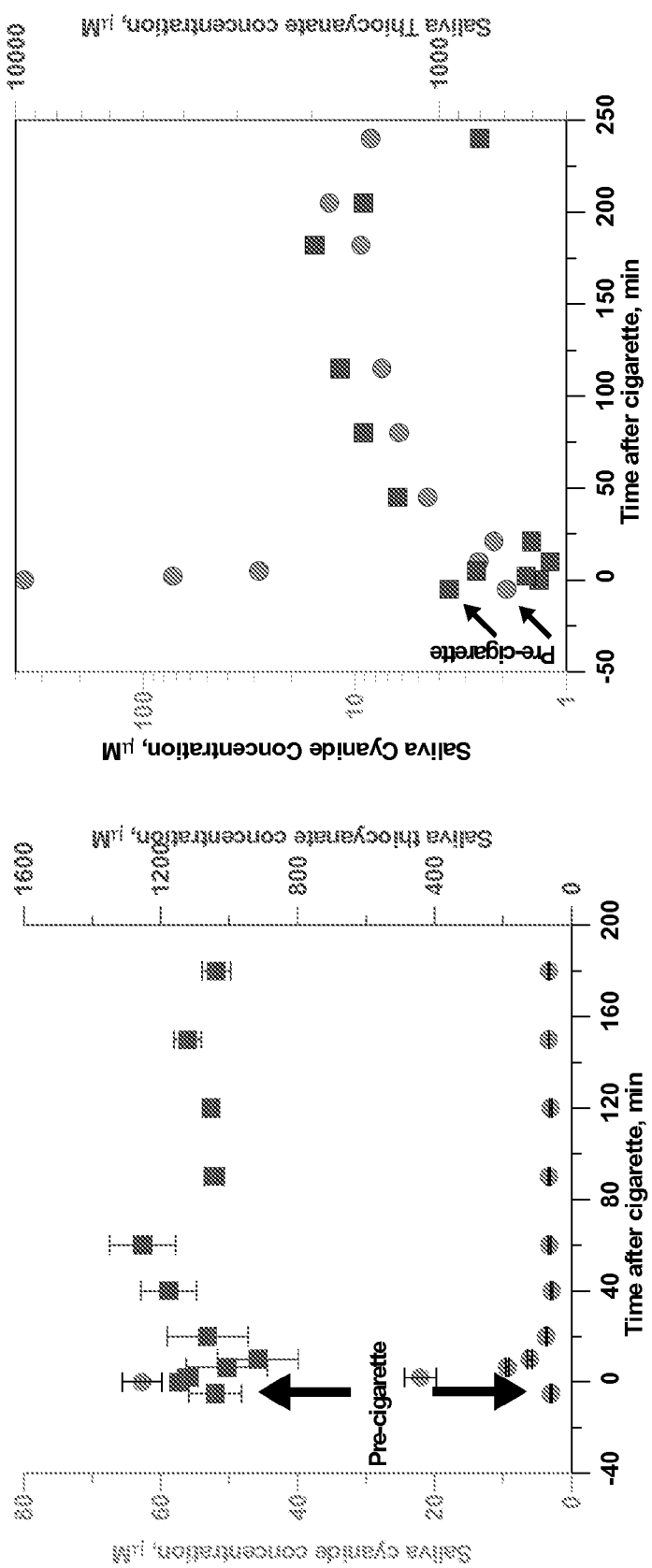
FIG. 21 illustrates the smoking experiment data.

FIG. 21 illustrates the smoking experiment data. Left is the data from a heavy smoker (~20 cigarettes/day). Right is the occasional smoker's data. In both cases, cyanide concentration is the scale on the left y axis and shown in circles and the thiocyanate concentration is the scale on the right y axis and shown in squares.

LED-Based Blood Cyanide Analyzer

Reagents. All chemicals used were reagent grade or better and 18.2 MΩ·cm Milli-Q water available from Millipore was used throughout. Pure cobinamide was produced by acid hydrolysis of cobalamin (available from Sigma-Aldrich) following Broderick et al (*J Biol. Chem.*, 2005, 280, 8678-8685). The stock cyanide solution was prepared by dissolving KCN in 1 mM NaOH and calibrated by published by the American Public Health Association and mentioned previously herein. It was stored refrigerated. The reagent and cyanide working solutions were prepared in 1 mM NaOH solution daily. The 0.1 M borate buffer solution was prepared by dissolving sodium borate ($Na_2B_4O_7 \cdot 10H_2O$, E.M. Science, CAS 1303-96-4) in Milli-Q water and adjusted to pH 9.00 with 2 M NaOH or HCl solution using ALTEX Φ71 pH meter (available from Beckman), which has been calibrated immediately before measurement by bracketing NIST-traceable pH 7 and 10 standard buffers.

Filter Pre-Treatment Procedure. The Fisher type 09-801AA filters were cut to ~7×7 mm square, and immersed in 1 mM cobinamide prepared in pH 9.00 borate buffer solution for 5 min, removed and then allowed to dry in clean air until they were completely dry. The prepared filters were kept in zippered storage bags and stored at room temperature in a sealed vial with a few pellets of NaOH to absorb any $CO_2$, which might neutralize the buffer. They were stable in this condition for week-long periods. In alternate embodiments, Whatman filters 1001-325 (Grade 1 qualitative cellulose filter, porosity 11 µm), 1002-042 (Grade 2 qualitative cellulose filter, porosity 8 µm) and 1005-325 (Grade 5 qualitative cellulose filter, porosity 2.5 µm) can be used. Additionally, the concentration of cobinamide in which filters are immersed can be anywhere from 0.5-2.5 mM.

Figure 22:
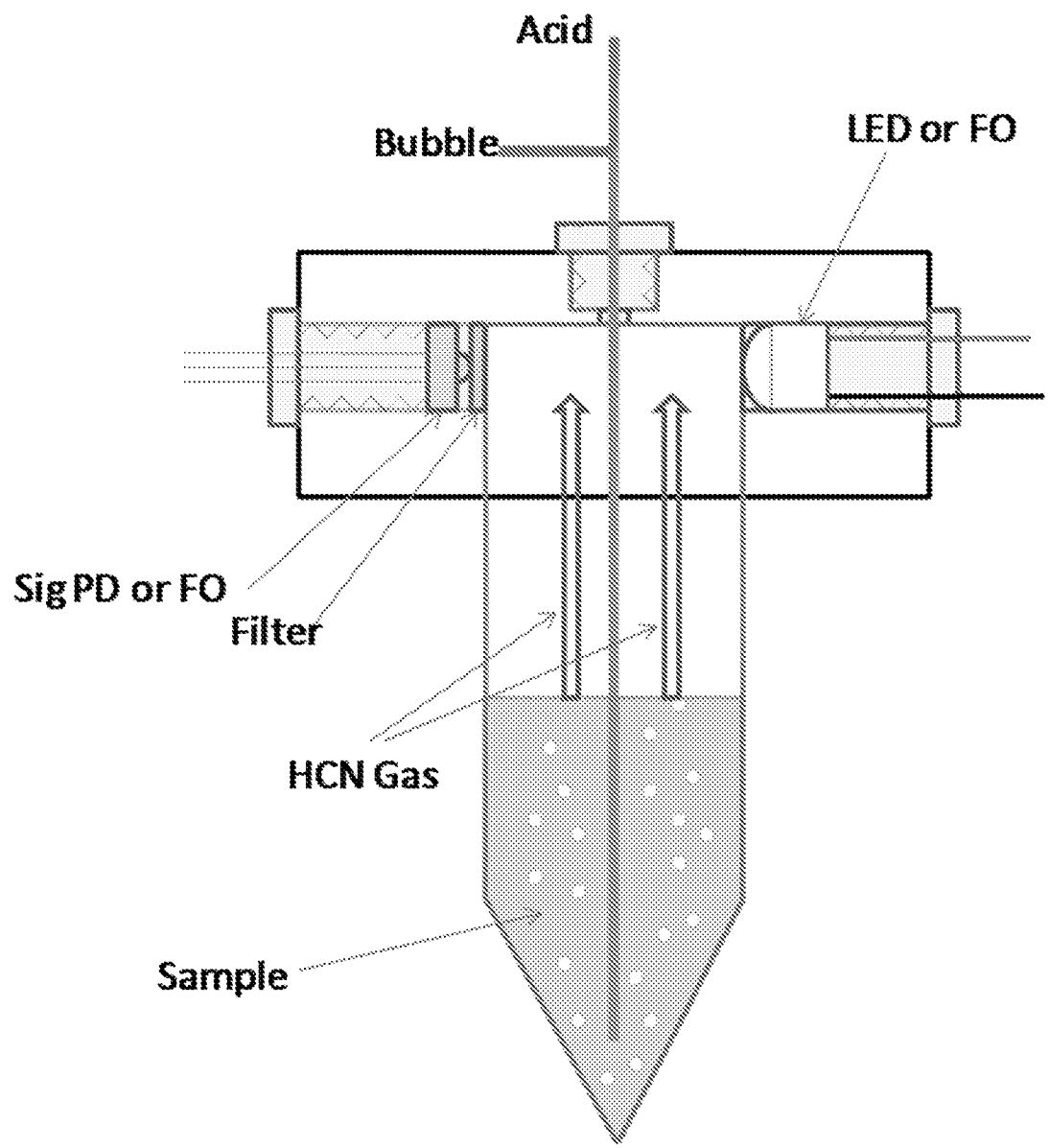
FIG. 22 illustrates an LED-based analyzer according to one embodiment.
Figure 23:
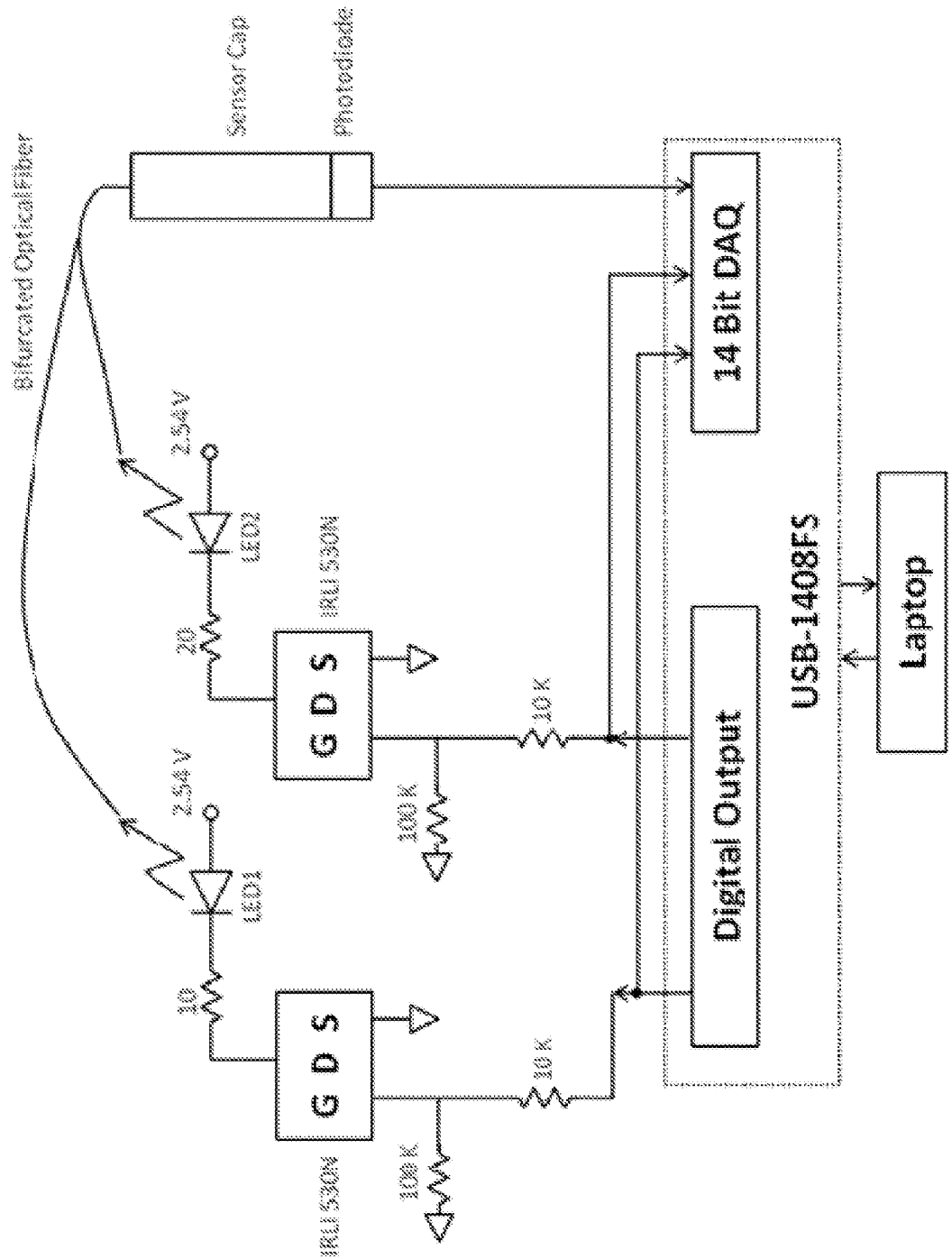
FIG. 23 illustrates the circuit of an analyzer according to one embodiment.
Figure 24:
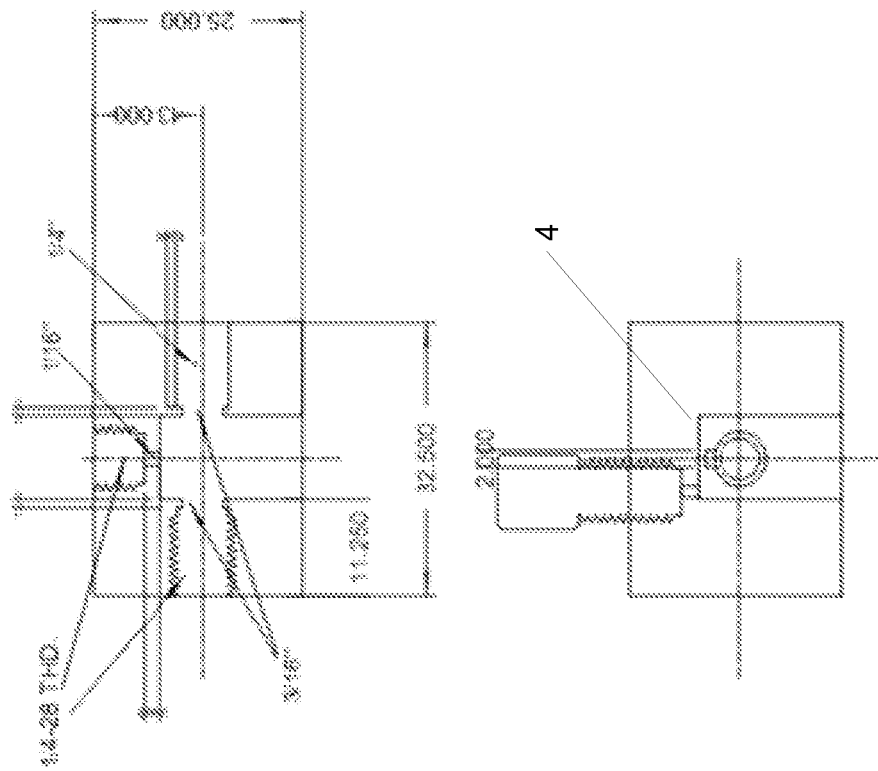
FIG. 24 is a structural drawing of an analyzer according to one embodiment.
Figure 24:
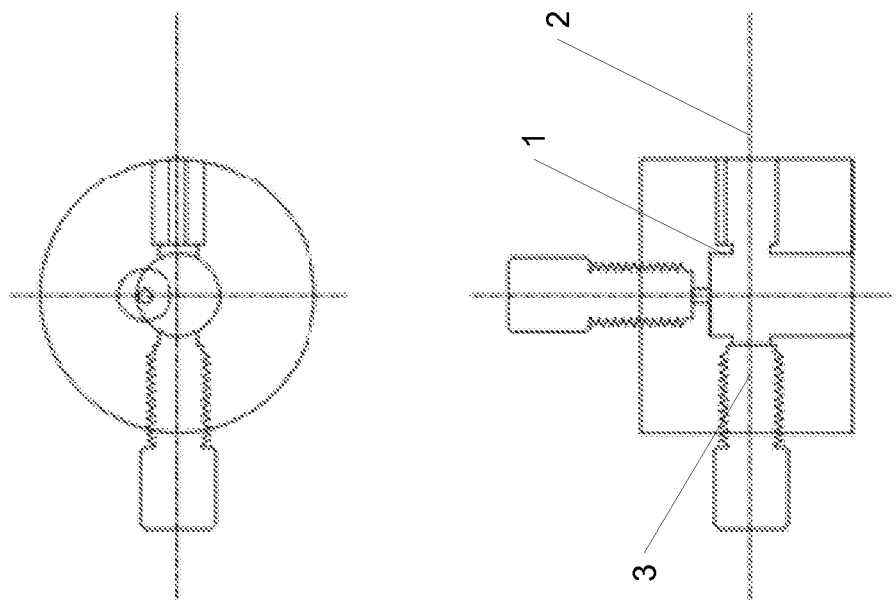
Figure 28:
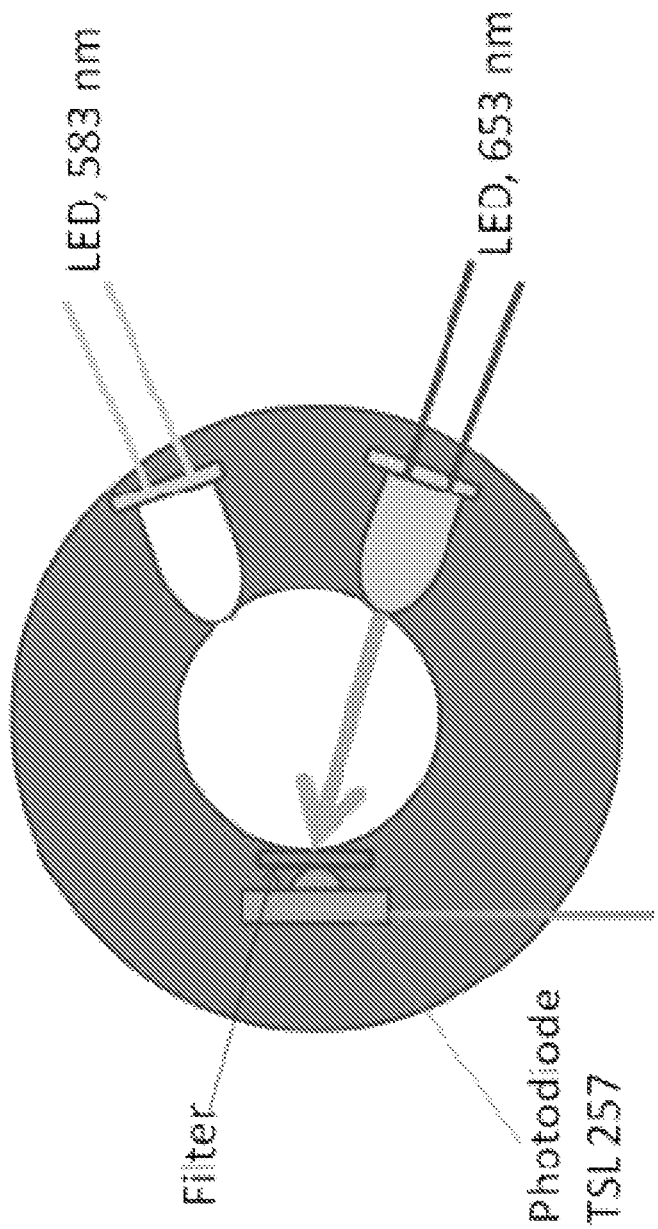
FIG. 28 illustrates an analyzer cap according to one embodiment.

Experimental Arrangements. The structure of the analyzer according to one embodiment is shown in FIG. 22. Normally, a 583 nm LED source (Hewlett-Packard HLMP 3850A, viewing angle)24°)was driven at a current of 10 mA, a 10Ω dropping resistor was used with a supply voltage of 2.1 V. A high sensitivity light to voltage converter (monolithic integrated photodiode-operational amplifier combination) TSL257 (available from Texas Advanced Optoelectronic Solutions) was used as detector. In an alternate embodiment, a CCD spectrophotometer can be used for detection. The detector output data were acquired with a 14-bit USB based data acquisition board USB-1408FS (available from Measurement Computing) using a 1 s RC filter. In the latter experiment, the position of 583 nm LED was occupied by a bifurcated fiber optic (FO, available from Dolan Jenner). The free distal end of the fiber was coupled to a 583 nm LED as signal and a 653 nm LED as reference, which were driven at 30 and 31 mA, respectively. The two LEDs were turned on and off alternately at 0.33 Hz (1.5 s for each) and controlled via an N-channel logic level MOSFET switch (IRLI530N available from International Rectifier) (circuit shown in FIG. 23). FIG. 24 illustrates the structural drawing of FIG. 22. The detector is affixed to the tip of a hollow rigid tubular holder with a ridge on the top of the holder tube with a notch machined on the top of it so that each time it is slid into the cap at position 2, it has the same orientation. First the filter disk is put in through the open aperture at position 1 and the detector holder is slid behind it and holds it in place. The aperture through which the filter is exposed to the open headspace in the vial is 3/16 in. in diameter and is 1 mm deep. No fiber optics were used so light loss was minimized. The LED was directly affixed with a nut in the aperture in position 3 and the emitter to detector distance was reduced. Changing the filter can be done reproducibly and is accomplished quickly and easily. The aperture for adding acid was off-center so that the tube passing through was not in the beam path. Another 5/32 in. hole was drilled for inserting another tube (SW 17, ZEUS Inc.) for pumping air to bubble through the sample. In one embodiment, the analyzer cap could be modified by direct fixation of signal and reference LED without fiber optics (FIG. 28), which could reduce the light loss and instrument cost and be applied as rapid, sensitive, specific and robust point of care (POC) blood cyanide analyzers for use in the field.

The software for data acquisition and LED on-off control was written in Labview 8.5 (National Instruments). For the spectrum experiment, the signal PD was replaced by a 1 mm diameter FO that coupled the light to a miniature USB 2000 CCD spectrophotometer (available from Ocean Optics). The 583 nm LED was replaced by a white LED (NSPW500BS available from Nichia), which had useful output over the 400-700 nm range. The 583 nm LED was driven at a current of 25 mA. A 10Ω dropping resistor was used with a supply voltage of 3.8 V.

Measurement Procedure. 1 mL bovine blood sample (VWR, defibrinated, P/N R100-0250, Lot #BP2912) spiked with cyanide solution was pipetted into a screwtop microvial (Axygen Scientific, P/N ST-200, capacity 2 mL). 100 µL ethanol was added as de-foamer. The vial was capped with the analyzer cap which has built in o-ring seals to seal on top of the vial. 0.1 mL 20% (v/v) $H_3PO_4$(EM) was added from the top tube by a 1 mL syringe. Air bubbles were delivered using a 50 mL syringe by hand for 1 min to facilitate acid and blood mixing. In an alternate embodiment, mixing is accomplished with a magnetic stirrer or by ultrasound. Simultaneous to the time the acid addition is begun, DAQ signal acquisition is initiated with a 1 Hz acquisition rate. It was found adding acid could lead to a mini pulse of the signal. After adding acid, the baseline might shift. Thus, the detector voltage at t=20 s, is taken to be the initial transmittance signal $I_0$. All other temporal detector output signals at non-zero values of t (recorded up to ~300 s) are taken as $I_t$ and the absorbance value $A_t$ is computed as log $I_0/I_t$.

Figure 25:
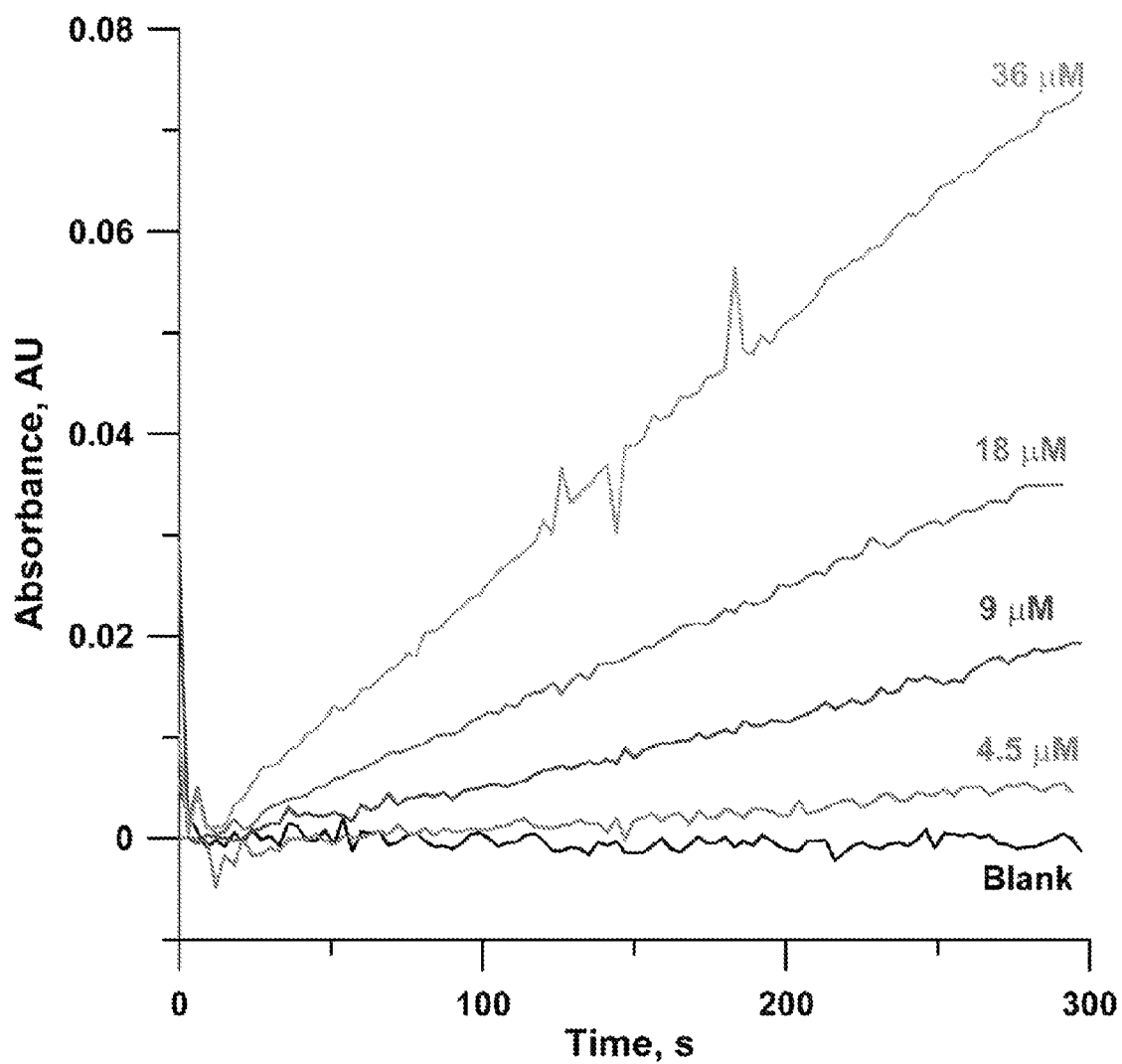
FIG. 25 illustrates response of the analyzer according to one embodiment.
Figure 26:
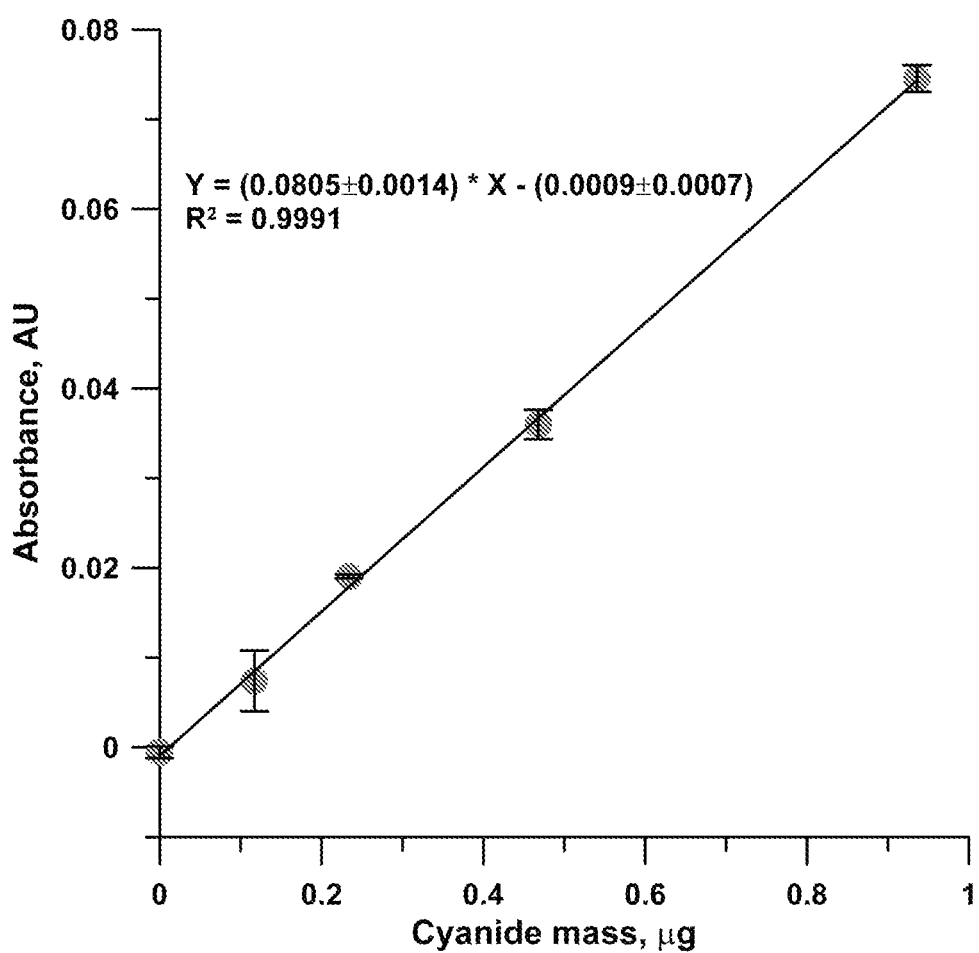
FIG. 26 illustrates a calibration curve of an analyzer according to one embodiment.

Performance. Response of the analyzer to 0-36 µM cyanide using 1 mL sample is shown FIG. 25. In order to widen the analytical range, smaller sample volumes, 0.2 and 0.5 mL, were also tested. The calibration curve with cyanide mass as x axis is FIG. 26. The relative standard deviation (RSD) was 1.09% using 9 µM spiked sample (n=5). The limits of detection (LODs), estimated from three times the standard deviation of the blank/divided by the calibration slope, were 2 µM for signal wavelength detection and 0.5 µM for dual wavelength detection.

Figure 27:
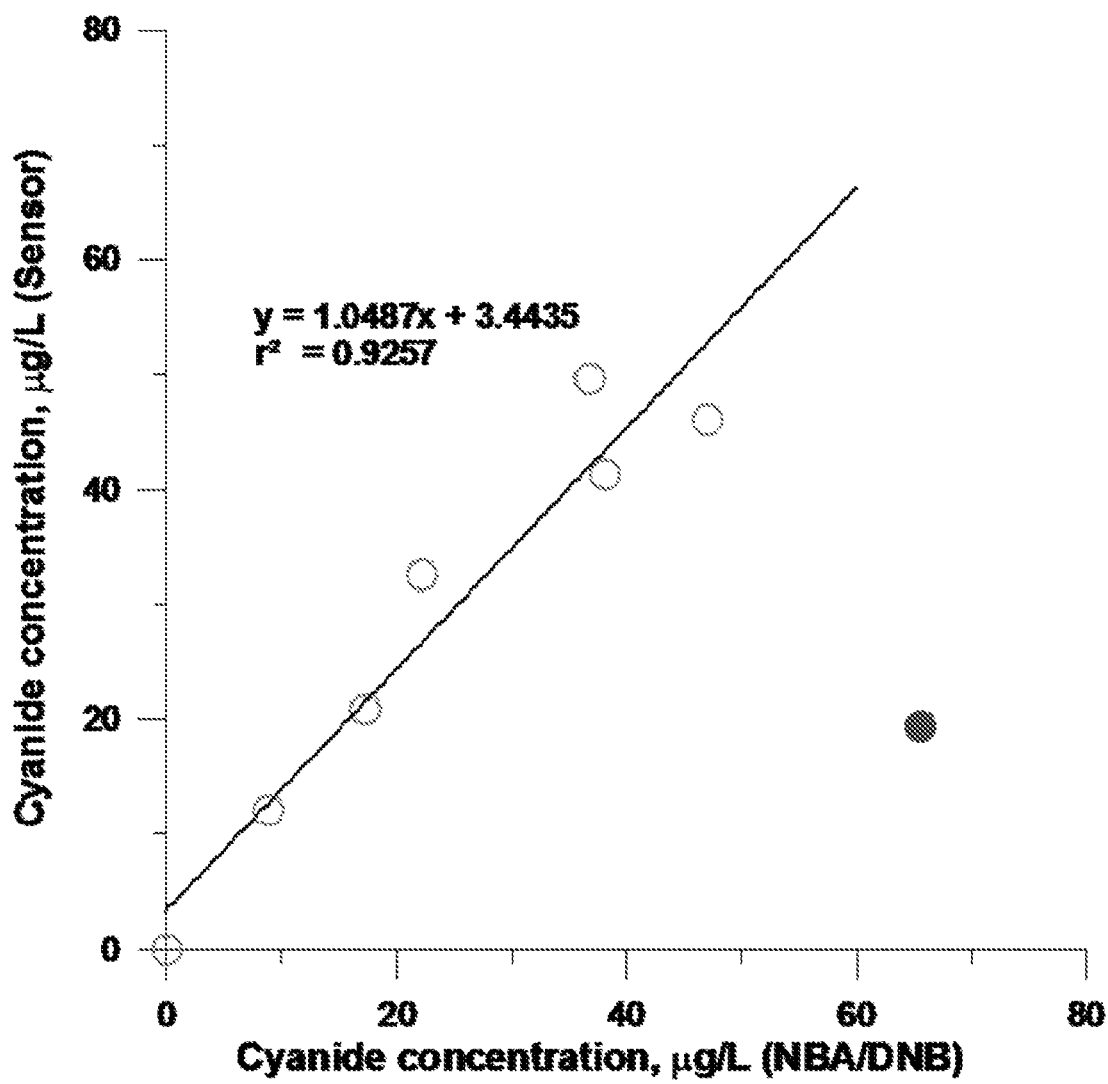
FIG. 27 illustrates the results of rabbit blood cyanide analysis with an analyzer according to one embodiment plotted against results obtained with NBA/DNB method.

Measurement of Cyanide in Rabbit Blood. The same samples tested previously (Example 1 results shown in FIG. 3) were tested using the LED-based analyzer as well. Because the sample volume was sufficient only for single analysis, in order to check the instrument stability, bovine blood samples spiked with cyanide were used as quality control (QC) sample. The recoveries of 3 QC samples are 94.23%, 95.03% and 91.84%, respectively. FIG. 27 illustrates the results plotted against the NBA/DNB results obtained in Example 1.

Portable Cyanide Sensor

Figure 29:
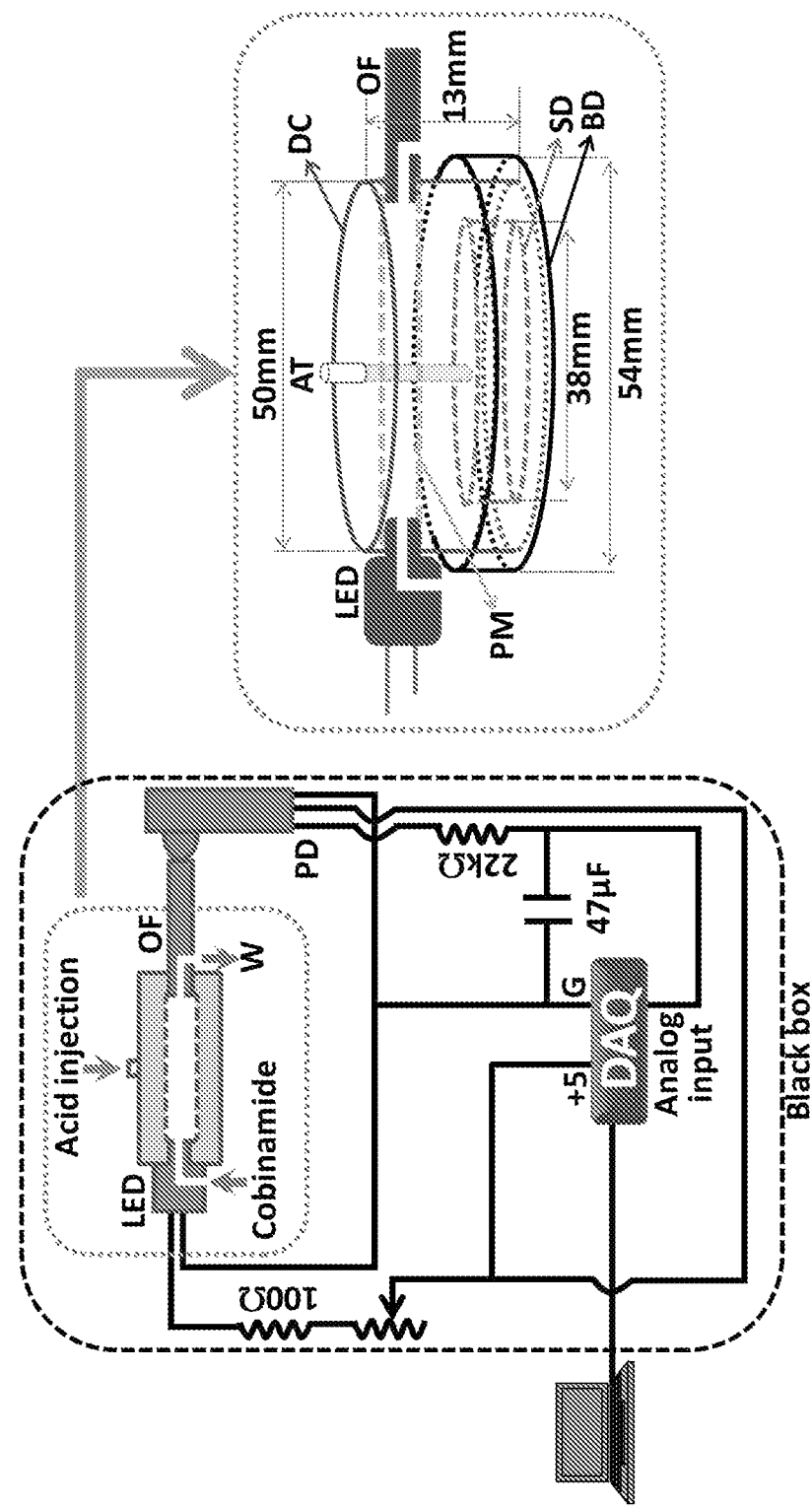
FIG. 29 illustrates a portable cyanide sensor according to one embodiment.
Figure 30:
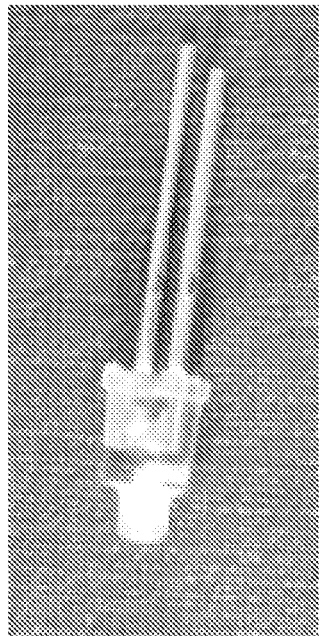
FIG. 30 illustrates LEDs used in the portable cyanide sensor according to one embodiment.
Figure 30:
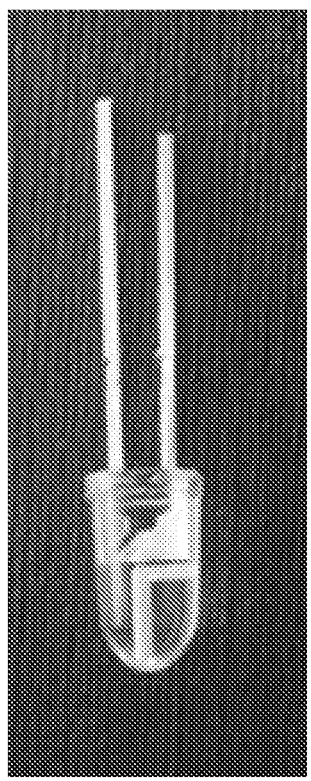

FIG. 29 illustrates a portable cyanide sensor. The disposable portion of the device has an outer Petri-dish—the top portion of this (35 mm dia) holds a porous membrane (PM) horizontally strung across it. The membrane is porous polypropylene membrane tube (PPMT) of 1.8 mm inner diameter. The flexibility of the PPMT allows it to fit tightly to the LED and the optical fiber. The membrane terminates in a 585 nm light emitting diode (LED) with a liquid outlet. A channel is drilled at a right angle through the optical path of the LED and the top of the LED is ground. The left image of FIG. 30 is before the machining and the right image is the LED after machining. The LED is attached in series with a 100Ω resistor and a potential meter to protect and control the LED's light intensity. The other end of the PPMT connects to an acrylic optical fiber (OF) (2 mm inner diameter) hooked to a photodiode and signal processing system. A channel was also drilled into the optical fiber at a right angle. Thus, the cobinamide solution could come into the PPMT from the LED right angle channel and exits to waste through the optical fiber right angle channel with no leakage. A TSL257 (www.taosinc.com) photodiode was connected as detector to the end of the optical fiber opposite the PPMT. The detector output data were acquired with a 14-bit USB based data acquisition board USB-1408FS available from Measurement Computing using a 1 s RC filter. (22 kΩ resistor and 47 µF capacitor).

The LED, PPMT and optical fiber were fixed on a petri dish of 50 mm inner diameter acting as detection cell (DC). Under the detection cell was a petri dish of 54 mm inner diameter (the "bottom" dish or BD). A smaller (i.d. =30 mm) petri-dish cover was put in the bottom dish under the detection cell as sample dish (SD). Thus the blood sample put into sample dish does not run into an undefined area of the bottom dish. On the center of detection cell, a whole is drilled for a PTFE tube (AT) to introduce acid into the sample dish. The acid can be a solid strong acid for facile packaging. Just before use, the seal on a syringe containing cobinamide solution is broken and cobinamide is introduced into the porous membrane tube. One mL of blood or other liquid sample is then injected through the top and the syringe left in place so the seal is maintained. The evolved HCN is absorbed by the cobinamide in the porous membrane tube that also functions as an optical cell. Low to sub-micromolar level cyanide measurement in blood is possible in a few minutes.

All chemicals used were at least analytical-reagent grade and 18.2 MΩ·cm Milli-Q water available from Millipore was used throughout. Pure cobinamide was produced by acid hydrolysis of cobalamin (available from Sigma-Aldrich) following Broderick et al (*J Biol. Chem.*, 2005, 280, 8678-8685). 0.02 mM cobinamide solution in 0.1 M borate buffer solution (pH=10.0, prepared by dissolving sodium borate ($Na_2B_4O_7 \cdot 10H_2O$, E.M. Science, CAS 1303-96-4) in Milli-Q water and adjusted to pH 10.00 with 2 M NaOH by using a pH meter (ALTEX Φ71, Beckman)) was prepared daily. The stock cyanide solution was prepared by dissolving KCN in 1 mM NaOH and stored refrigerated. Defibrinated bovine/calf blood (Code: R100-0050, www.rockland-inc.com) was used as the blank blood sample and spiked with cyanide for experimental optimization and performance calculation. Rabbit blood samples were obtained from ongoing studies conducted at the University of California, Irvine, according to NIH Guidelines for the Care and Use of Laboratory Animals, and approved by the Institutional Animal Care and Use Committee.

Prior to beginning the experiment, the LED is turned off and the black box is closed and the DAQ opened to record the dark current signal for about 200 second, the average of these signals is determined as $I_d$. The black box cover was opened and 1 mL of blood sample was injected into the sample dish. The sample dish was placed into the bottom dish. The sample dish is shielded from the detection cell, which is fixed on the black box cover. The porous polypropylene tube (PP tube) is filled with the cobinamide solution with the black box closed. After that, the DAQ was opened to record the signal, $I_0$, for 60 seconds. The acid is injected from the top of the black box into the system to release the cyanide from sample. The cyanide was captured by the cobinamide in the PPMT and thus the cobinamide solution changed color, which caused a signal, $I_t$, which was recorded by the DAQ. Signals are recorded for at least 160 s. After signal recordation the black box was opened for release the remains cyanide in the detection cell and change another sample dish for next running.

Refreshing the cobinamide in the PPMT induces a slight fluctuation in the signal and thus $I_0$ was for time 50-60 seconds. To eliminate dark current influence $I_d$ was substracted from both $I_0$ and $I_t$. Absorbance, A, was determined by the following formula, $A=\log((I_0-I_d)/(I_t-I_d))$.

Figure 31:
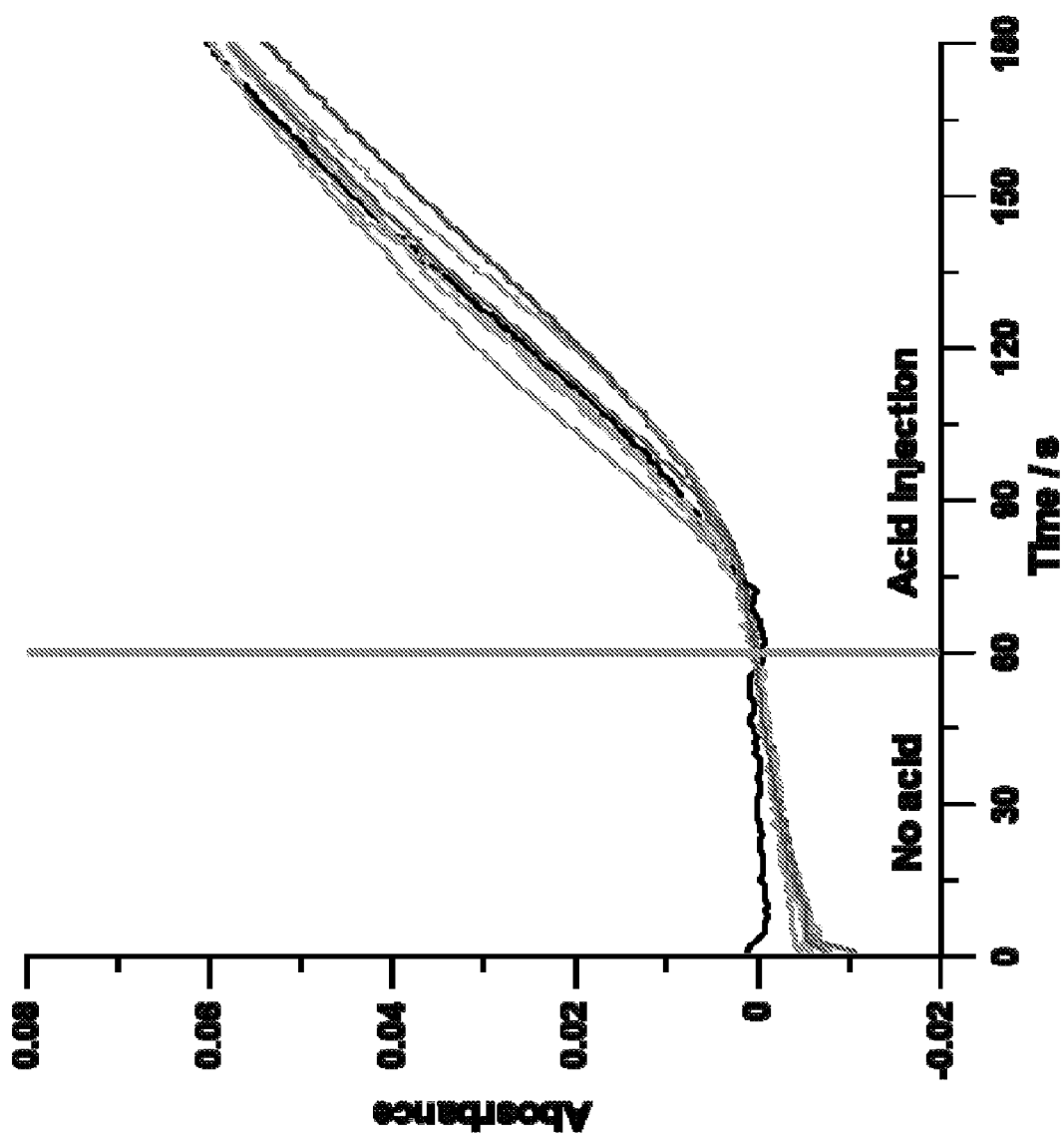
FIG. 31 illustrates continuous detection of 2 μM of cyanide spiked bovine blood samples with the portable cyanide sensor of FIG. 29.
Figure 32:
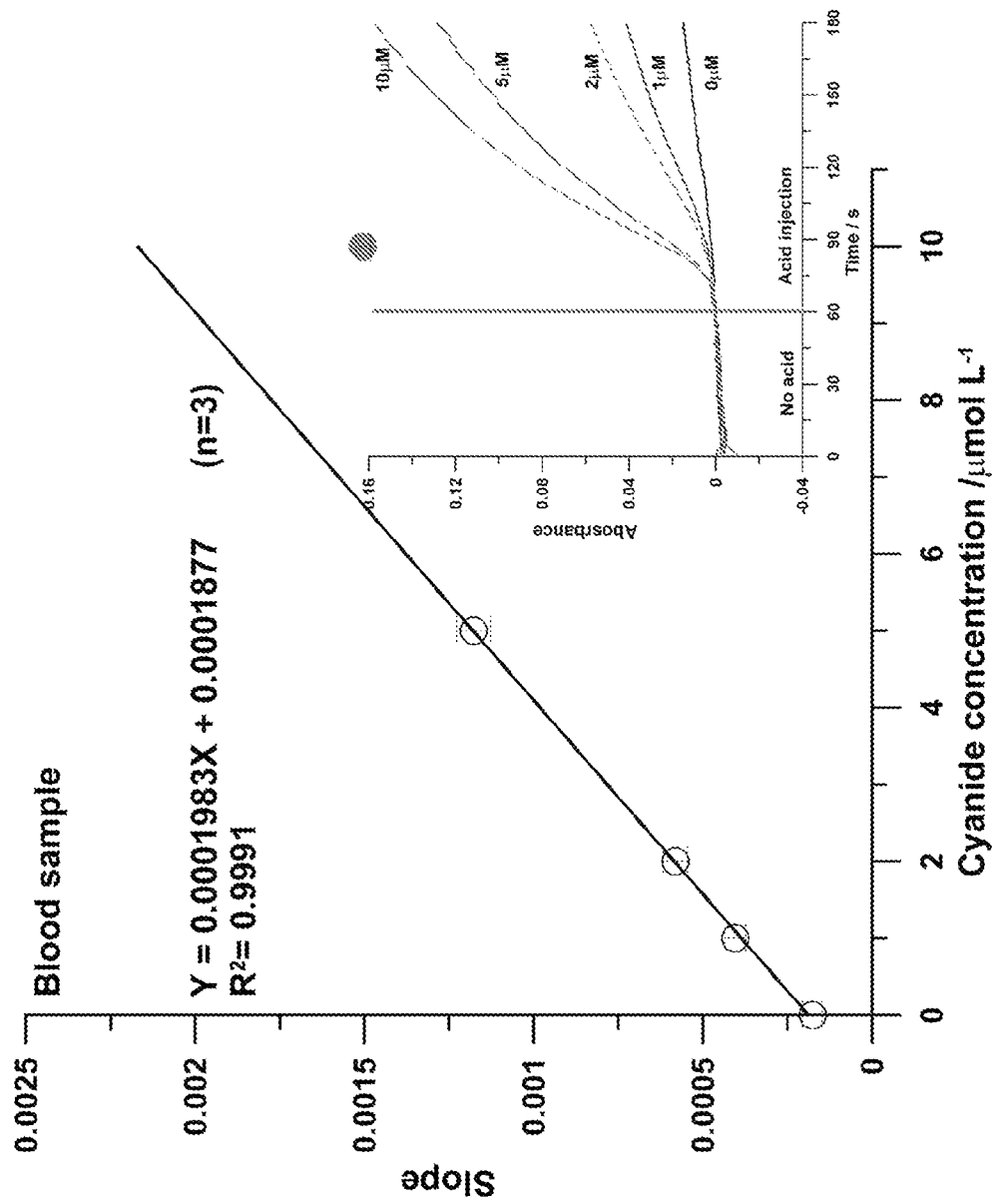
FIG. 32 illustrates the calculation curve of bovine blood samples measured with the portable cyanide sensor of FIG. 29.

Using 30% (v/v) of $H_3PO_4$ for to release cyanide from the samples, 20 µM of cobinamide solution in 0.01M of borate buffer (pH=10) as cyanide absorbent and colorimetric vehicle, the relative standard deviations (RSD) and limit of detections (LOD) of blood sample and water sample were calculated. Seven determinations of 2 μM cyanide in bovine blood are shown in FIG. 31, accounting the slope of 100 s to 160 s, the received RSD is 3.6% for the seven determinations. The bovine blood spiked with 0 to 10 μM cyanide was detected by this cyanide detector and the results are shown in FIG. 32. Limit of detection was 0.15 μM ($3*S.D._{blank}/k$, n=7), linear range was from 0.5 μM to 5 μM and the determination coefficient was ($R^2$) 0.9991 for cyanide detection in 1 mL of bovine blood sample.

Figure 33:
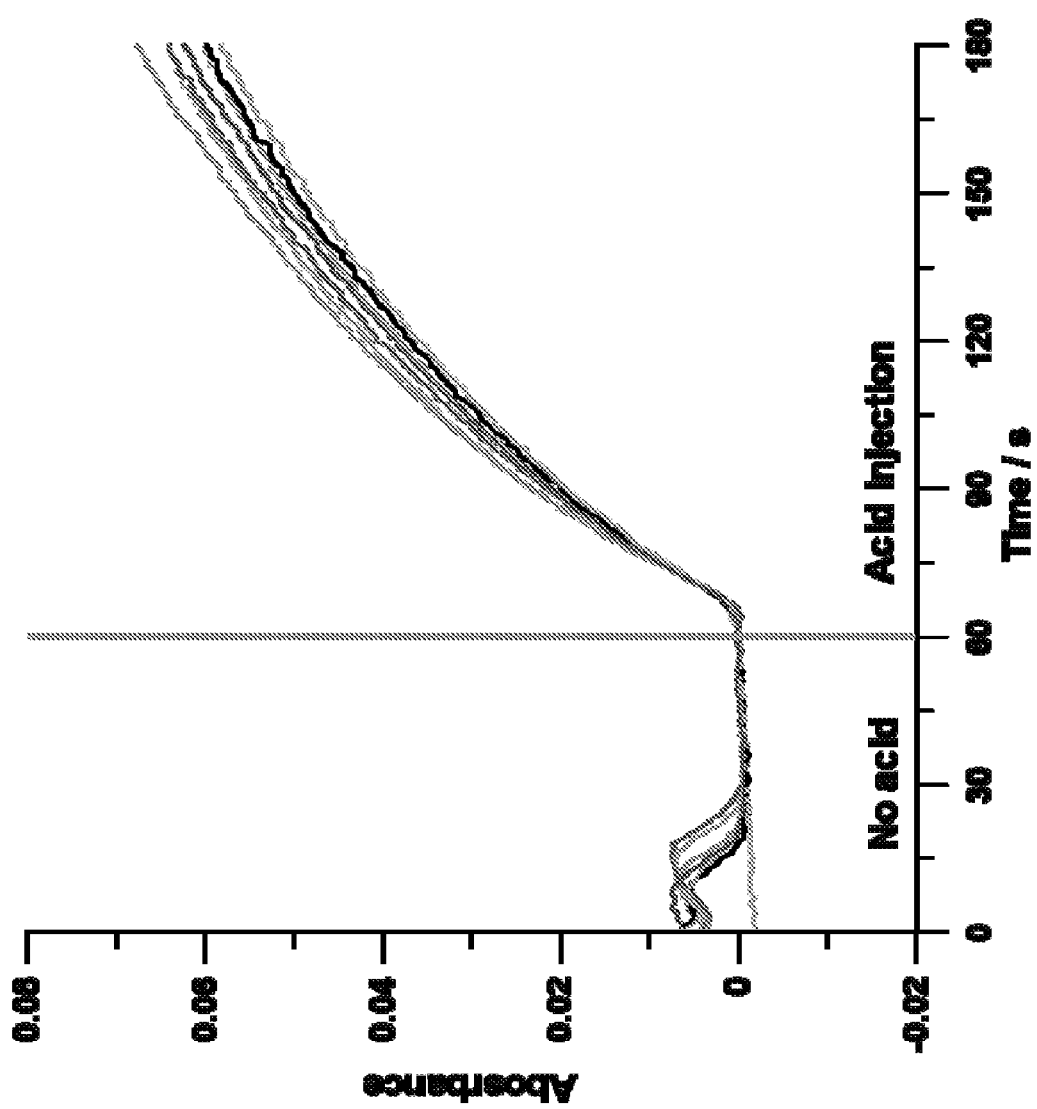
FIG. 33 illustrates the continuous detection of 2 μM of cyanide spiked water samples with the portable cyanide sensor of FIG. 29.
Figure 34:
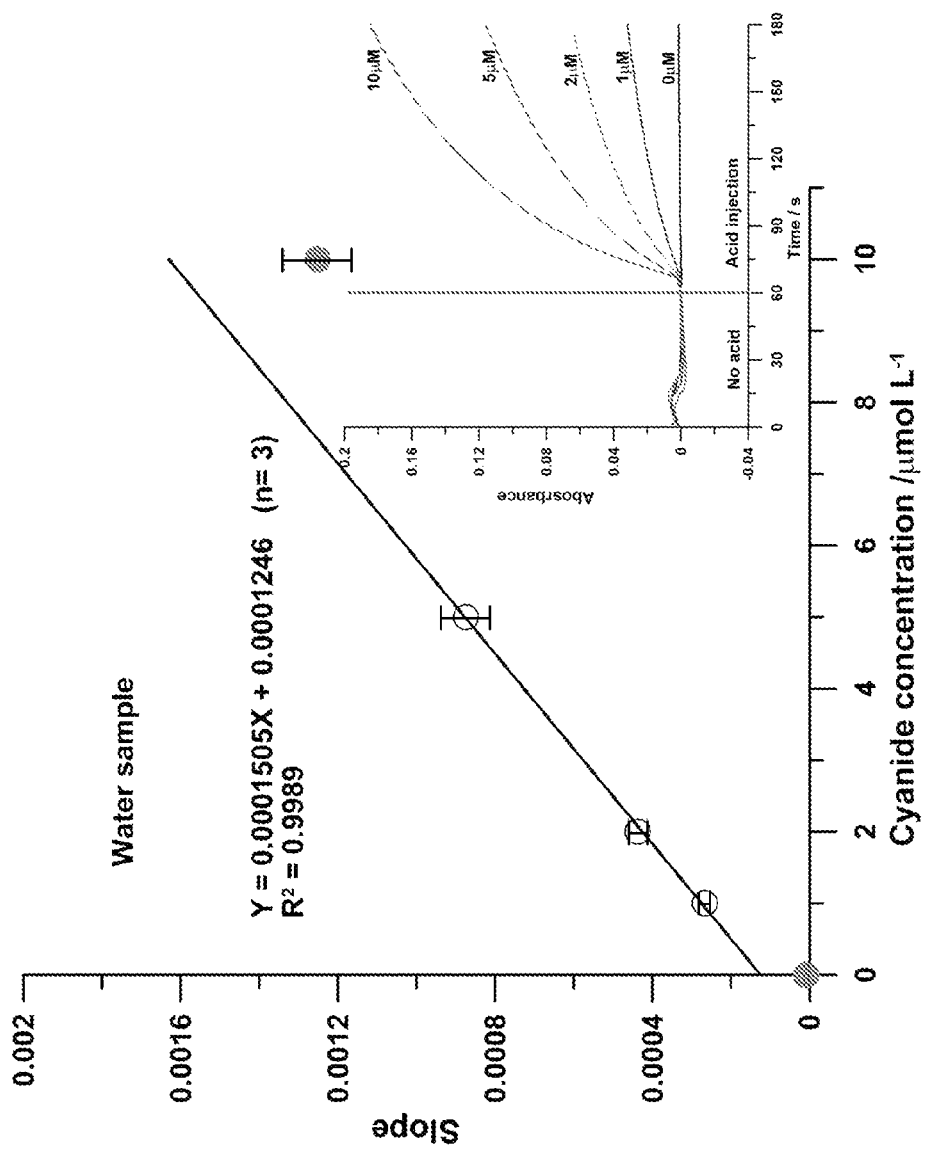
FIG. 34 illustrates the calculation curve of water samples measured with the portable cyanide sensor of FIG. 29.

Cyanide in water samples was also analyzed as shown in FIG. 33. 2 μM cyanide in water sample was determined seven times. RSD value was 4.7% (n=7, 2 μM of cyanide). FIG. 34 shows the determination of 0 to 10 μM cyanide in 1 mL water samples. The determined LOD was 0.047 μM, the linear range was 0.15 μM to 5 μM and the determination coefficient ($R^2$) was 0.9989.

Porous-membrane-based Device for Measuring Cyanide in Breath

Figure 35:
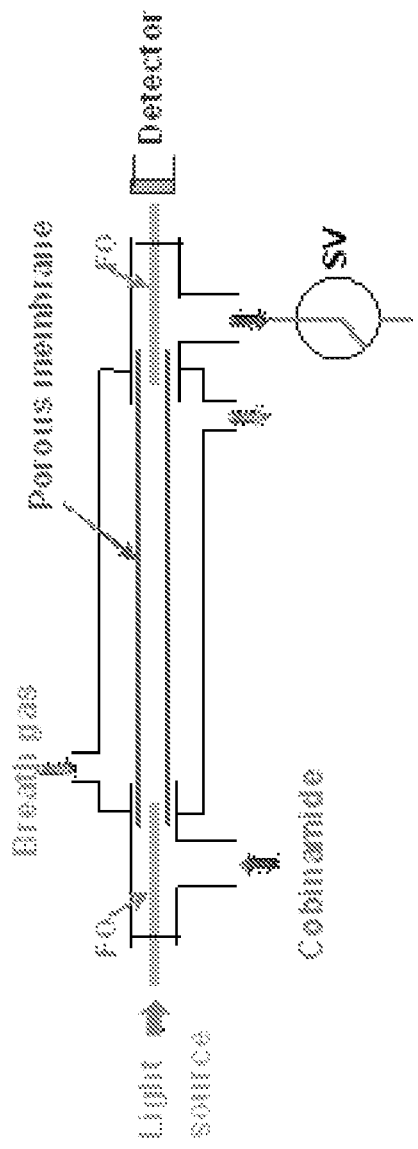
FIG. 35 illustrates a porous-membrane-based analyzer according to one embodiment.

Porous membrane tubes are alternatives to LCW's and can be superior for choromogenic gas measurement applications. FIG. 35 illustrates a porous-membrane-based device for measuring cyanide in breath. SV is a shut-off valve; when opened, fresh cobinamide fills the membrane. Light from an LED is transmitted to a photodiode detector by optical fibers (FO). Exhaled air enters the chamber, and cyanide gas in the breath diffuses through the porous membrane, reacting with the cobinamide and the absorbance change is monitored.

To generate HCN gas for calibration potassium cyanide is added to sulfuric acid. After establishing the temperature dependent equilibrium of gaseous HCN over a wide pH and temperature range, the concentration of cyanide gas in the generating system is determined by collecting the gas in alkali and measuring the cyanide in the liquid core waveguide based analyzer described above.

Figure 36:
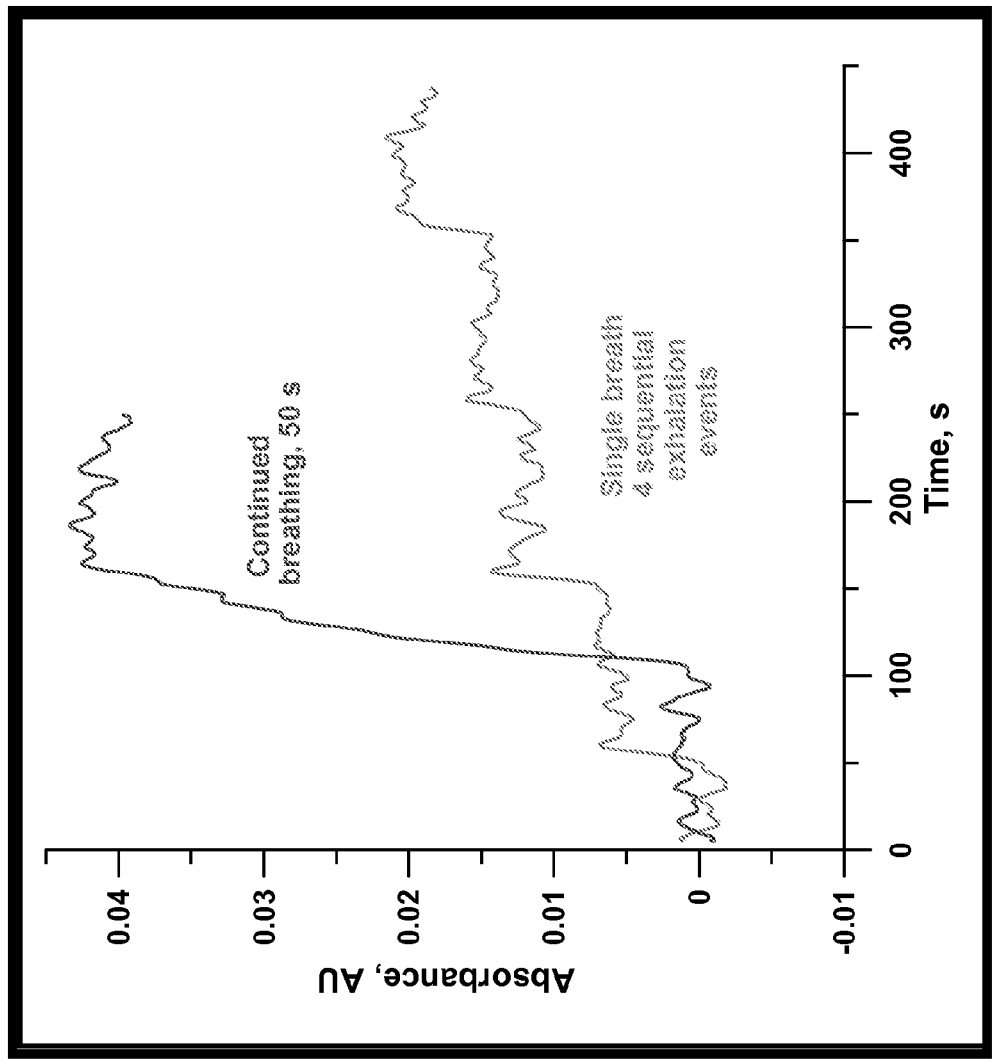
FIG. 36 illustrates measurement of breath cyanide in a non-smoking subject.

Using the porous-membrane-based device, breath HCN concentrations in three non-smoking subjects was measured. The measurements ranged from ~3 parts per billion by volume (ppbv) to 35.4±1.4 ppbv. These values fall within the 0-62 ppbv range reported in the literature for non-smoking subjects. In one of the subjects, we measured breath cyanide concentrations on four separate days, and found the following values: 24.4±2.6, 16.3±1.2, 28.0±0.5, 31.0±0.5, and 29.1±0.9 ppbv (mean±SD of three measurements). Thus, although day-to-day variability exists, it is relatively small. FIG. 36 illustrates measurement of breath cyanide in a non-smoking subject either as four separate exhalations or by continuous exhalation over 50 sec.

Figure 37:
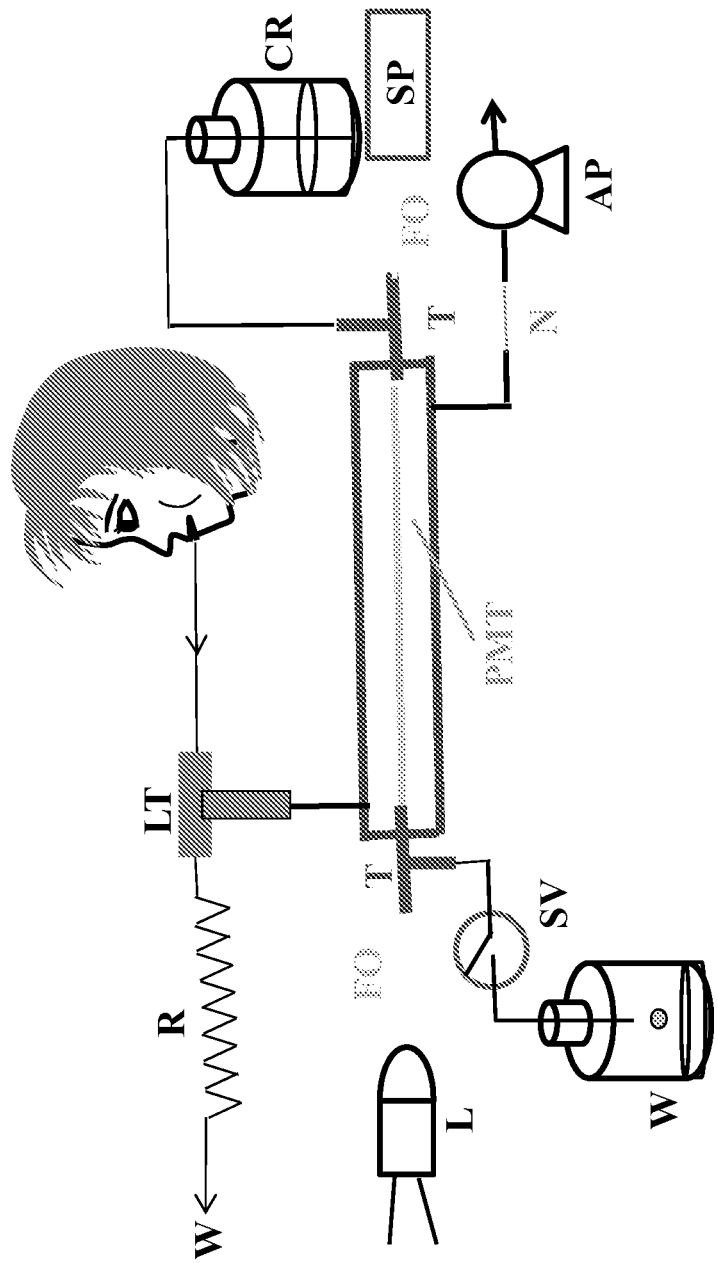
FIG. 37 illustrates a porous-membrane-based device in more detail according to one embodiment.

FIG. 37 illustrates a porous membrane-based device in more detail. The subject exhales through large tee LT and modest restrictor R to vent W. When the sampling sequence is initiated by pressing a button, air pump AP draws a portion of the breath sample through the device. Needle restrictor N acts as a critical orifice and holds the flow rate constant. The pump automatically shuts off after 10 s. Porous membrane tube PMT is filled by opening solenoid valve SV with fresh cobinamide reagent CR via tees T, with old reagent going to waste W. The tees accommodate acrylate fiber optics FO connected respectively to one or more different wavelength light emitting diodes L that are alternately pulsed and read at the other end by a signal photodiode SP. Data collection and processing electronics (not shown in this schematic) calculate the slope of the absorbance rise with time, and, based on a calibration plot stored in memory, digitally displays the cyanide concentration and stores it with date and time.

The invention claimed is:

1. A method for determining an amount of cyanide, comprising:
    contacting a sample comprising cyanide with a cobinamide or monocyanocobinamide;
    reacting the cyanide with the cobinamide or monocyanocobinamide resulting in cyanide bound to a portion of the cobinamide or monocyanocobinamide;
    exposing the sample to light;
    measuring an absorbance of the light by the sample wherein the measured absorbance differentiates between cyanide bound to the portion of the cobinamide or monocyanocobinamide and a remainder of cobinamide or monocyanocobinamide; and
    determine the amount of cyanide based on the measured absorbance.

2. The method of claim 1, wherein the light has a first wavelength of about 300 nm to about 600 nm.

3. The method of claim 1, wherein the light has a first wavelength of about 348 nm or about 366 nm.

4. The method of claim 1, wherein the light has a first wavelength of about 366 nm.

5. The method of claim 4 further comprising measuring the absorbance of light having a second wavelength of about 505 nm by the sample.

6. The method of claim 1, wherein the light has a first wavelength of about 490 nm to about 590 nm.

7. The method of claim 1, wherein the light has a first wavelength of about 580 nm.

8. The method of claim 7 further comprising measuring the absorbance of light having a second wavelength of about 505 nm by the sample.

9. The method of claim 1, wherein the light has a first wavelength of about 562 nm.

10. The method of claim 9 further comprising measuring the absorbance of light having a second wavelength of about 505 nm by the sample.

11. The method of claim 1 wherein the light has a first wavelength of 505 nm.

12. The method of claim 1 wherein the light has a first wavelength selected from the group consisting of about 348 nm, about 366 nm, about 505 nm, about 562 nm and about 580 nm.

13. The method of claim 1 wherein the cobinamide or monocyanocobinamide comprises hydroxoaquocobinamide, dihydroxocobinamide or aquocyanocobinamide.

14. The method of claim 1 wherein contacting the sample comprising cyanide with a cobinamide or a monocyanocobinamide comprises contacting the sample with a membrane comprising cobinamide or a monocyanocobinamide.

15. The method of claim 1 wherein the sample comprises air, water, blood or saliva.

16. The method of claim 1, wherein the amount of cyanide in the sample is about 0.25 nmol or greater.

17. The method of claim 16, wherein the amount of cyanide is about 0.25 nmol.

18. The method of claim 16, wherein the amount of cyanide is about 0.5 nmol or greater.

19. A surface for detecting cyanide comprising an effective amount of cobinamide or monocyanocobinamide wherein the surface or a portion thereof changes color from orange to violet upon contact with a sample comprising cyanide.

20. The surface of claim 19, wherein the surface is cobinamide-impregnated paper.

21. The surface of claim 19, wherein the surface is a cobinamide-impregnated porous membrane.

22. A method of determining an amount of cyanide in a sample, comprising:
- adding a sample comprising cyanide to a carrier;
- moving the sample and the carrier to a mixing coil comprising cobinamide or monocyanocobinamide;
- allowing the cobinamide or monocyanocobinamide and the sample to react resulting in cyanide bound to a portion of the cobinamide or monocyanocobinamide;
- exposing the sample to light;
- measuring an absorbance of light by the sample and the carrier wherein the measured absorbance differentiates between cyanide bound to the portion of the cobinamide or monocyanocobinamide and a remainder of cobinamide or monocyanocobinamide; and
- determining the amount of cyanide in the sample based on the measured absorbance.

23. The method of claim 22 wherein the light has a first wavelength selected from the group consisting of 366 nm, 505 nm, 562 nm and 580 nm.

24. The method of claim 22 wherein the cobinamide or monocyanocobinamide comprises hydroxoaquocobinamide, dihydroxocobinamide or aquocyanocobinamide.

* * * * *